US007896801B2

(12) United States Patent
Uchimura et al.

(10) Patent No.: US 7,896,801 B2
(45) Date of Patent: Mar. 1, 2011

(54) ENDOSCOPE WITH RIGIDITY VARIATION SECTION

(75) Inventors: Sumihiro Uchimura, Sagamihara (JP); Akira Taniguchi, Hachioji (JP); Fumiyuki Onoda, Tama (JP); Toshiaki Noguchi, Tachikawa (JP); Katsuya Suzuki, Sagamihara (JP)

(73) Assignee: Olympus Corporation, Tokyo (JP)

( * ) Notice: Subject to any disclaimer, the term of this patent is extended or adjusted under 35 U.S.C. 154(b) by 1168 days.

(21) Appl. No.: 11/585,300

(22) Filed: Oct. 19, 2006

(65) Prior Publication Data
US 2007/0038028 A1 Feb. 15, 2007

Related U.S. Application Data

(63) Continuation of application No. PCT/JP2005/007458, filed on Apr. 19, 2005.

(30) Foreign Application Priority Data

Apr. 22, 2004 (JP) ................... 2004-127271

(51) Int. Cl.
*A61B 1/005* (2006.01)
(52) U.S. Cl. ........................ 600/144; 600/131
(58) Field of Classification Search .................. 600/144, 600/131
See application file for complete search history.

(56) References Cited

U.S. PATENT DOCUMENTS

| 5,357,979 | A | * | 10/1994 | Imran | 600/585 |
|---|---|---|---|---|---|
| 5,800,421 | A | * | 9/1998 | Lemelson | 604/891.1 |
| 5,976,074 | A | * | 11/1999 | Moriyama | 600/144 |
| 6,203,494 | B1 | * | 3/2001 | Moriyama | 600/144 |
| 6,491,663 | B1 | * | 12/2002 | Lemelson | 604/103.02 |
| 6,562,021 | B1 | * | 5/2003 | Derbin et al. | 604/523 |
| 6,672,338 | B1 | * | 1/2004 | Esashi et al. | 138/119 |
| 6,790,173 | B2 | * | 9/2004 | Saadat et al. | 600/114 |
| 6,882,086 | B2 | * | 4/2005 | Kornbluh et al. | 310/328 |
| 6,891,317 | B2 | * | 5/2005 | Pei et al. | 310/328 |
| 7,223,329 | B2 | * | 5/2007 | Esashi et al. | 205/114 |
| 2002/0175594 | A1 | * | 11/2002 | Kornbluh et al. | 310/317 |
| 2003/0069475 | A1 | | 4/2003 | Banik et al. | |
| 2004/0034279 | A1 | | 2/2004 | Arai et al. | |
| 2004/0054254 | A1 | * | 3/2004 | Miyake | 600/104 |
| 2004/0193014 | A1 | * | 9/2004 | Miyagi et al. | 600/146 |
| 2005/0006009 | A1 | * | 1/2005 | Esashi et al. | 148/518 |
| 2005/0165439 | A1 | * | 7/2005 | Weber et al. | 606/191 |
| 2005/0261549 | A1 | * | 11/2005 | Hewit et al. | 600/114 |

FOREIGN PATENT DOCUMENTS

| EP | 1 010 440 A2 | 6/2000 |
|---|---|---|
| JP | 05-237056 | 9/1993 |
| JP | 06-181882 | 7/1994 |
| JP | 2000-166860 | 6/2000 |
| JP | 2000-233027 | 8/2000 |
| JP | 2002-330924 | 11/2002 |
| JP | 2003-079566 | 3/2003 |
| JP | 2003-225197 | 8/2003 |
| JP | 2003-275168 | 9/2003 |

* cited by examiner

*Primary Examiner* — John P Leubecker
(74) *Attorney, Agent, or Firm* — Scully, Scott, Murphy & Presser, PC

(57) ABSTRACT

An endoscope is provided wherein a variable rigidity portion is not restricted by a physical mechanism, and which allows a surgeon, in performing a rigidity varying operation, to operate the rigidity varying operation along with other operations without releasing inputting sections. The endoscope of the invention includes an inserting section and an operating section. The inserting section has variable-rigidity actuators. The operating section has a rigidity-variation controlling section, a trackball, and scope switches.

24 Claims, 26 Drawing Sheets

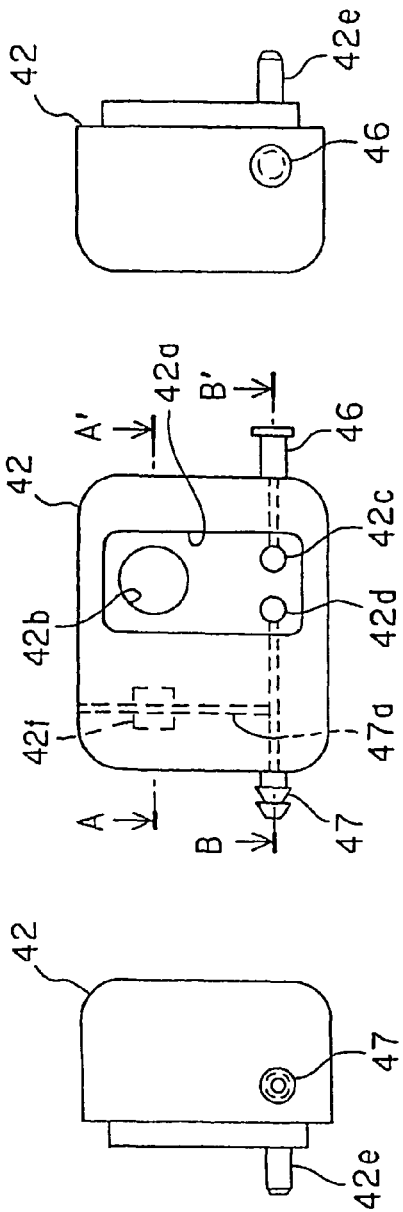
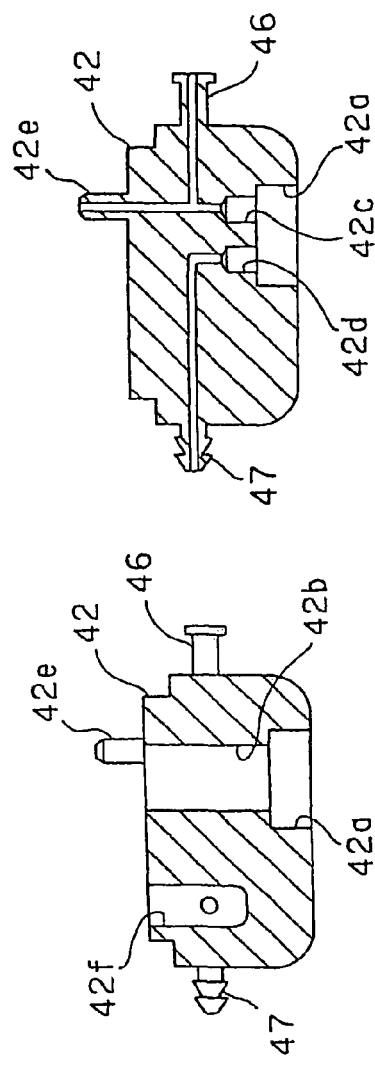

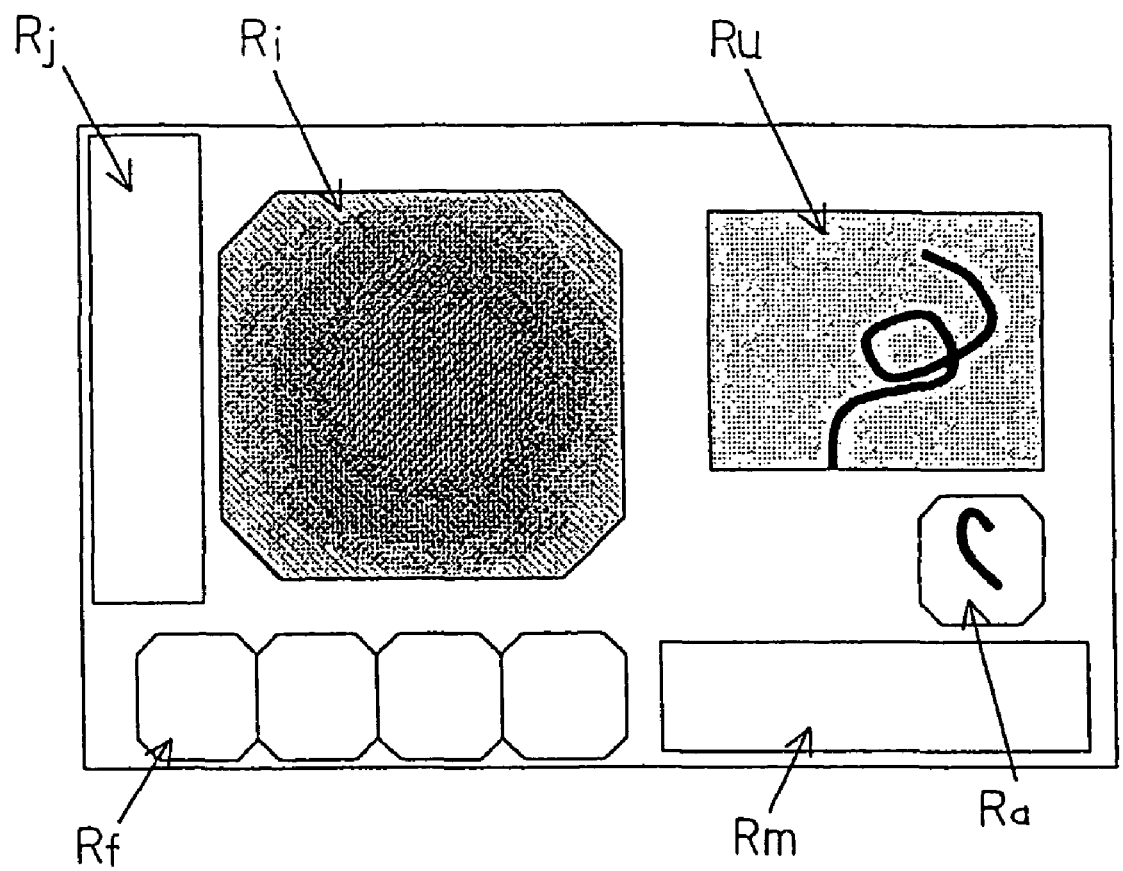

ENDOSCOPE WITH RIGIDITY VARIATION SECTION

CROSS REFERENCE TO RELATED APPLICATION

This application is a continuation application of PCT/JP2005/007458 filed on Apr. 19, 2005 and claims benefit of Japanese Application No. 2004-127271 filed on Apr. 22, 2004, the contents of which are incorporated by this reference.

BACKGROUND OF THE INVENTION

1. Field of the Invention

The present invention relates to an endoscope which is inserted into a body cavity and the like to perform endoscopy and the like.

2. Description of the Related Art

Conventionally, endoscopes have been widely used in medical and industrial fields and so on. For example, in the medical field, endoscopes are used when performing various treatments to a diseased part of a body cavity portion and tissues and the like of a living body. When performing the various treatments to the diseased part by using an endoscope, it is necessary to smoothly insert the endoscope into the curved body cavity of the living body. For this reason, an inserting section of the endoscope usually has flexibility. However, there was a problem that when the inserting section only has flexibility, operations at hand-side of the inserting section are not fully transmitted to a distal end side thereof, thus preventing the direction of the distal end side of the inserting section from being settled, resulting in the endoscope incapable of being smoothly inserted into the curved body cavity of the living body. To solve such a problem, Japanese Patent Application Laid-Open No. 2002-330924, for example, proposes an endoscope wherein an inserting section is provided with a flexible tube portion and a variable rigidity mechanism, and wherein an operating section provided with an adjusting knob capable of operating the variable rigidity mechanism by an operation at hand.

SUMMARY OF THE INVENTION

An endoscope according to the present invention comprises an inserting section and an operating section, wherein the inserting section comprises at a plurality of positions a variable-rigidity mechanism capable of varying rigidity when applied with a voltage, and wherein the operating section comprises: a rigidity-variation controlling section for varying rigidity by controlling the variable-rigidity mechanism; and a rigidity-variation operating section for making a direction for varying rigidity to the rigidity-variation controlling section.

BRIEF DESCRIPTION OF THE DRAWINGS

FIG. 7A is a front view of the AWS adaptor 42;

FIG. 7B is a left side view of the AWS adaptor 42;

FIG. 7C is a right side view of the AWS adaptor 42;

FIG. 7D is a cross-sectional view taken along A-A' of FIG. 7A;

FIG. 7E is a cross-sectional view taken along B-B' of FIG. 7A;

FIG. 16A is a diagram showing an example of an image to be displayed on a monitor right after the endoscope system is powered on;

DETAILED DESCRIPTION OF PREFERRED EMBODIMENTS

With reference to the drawings, an embodiment of the present invention will be described below.

Figure 1:
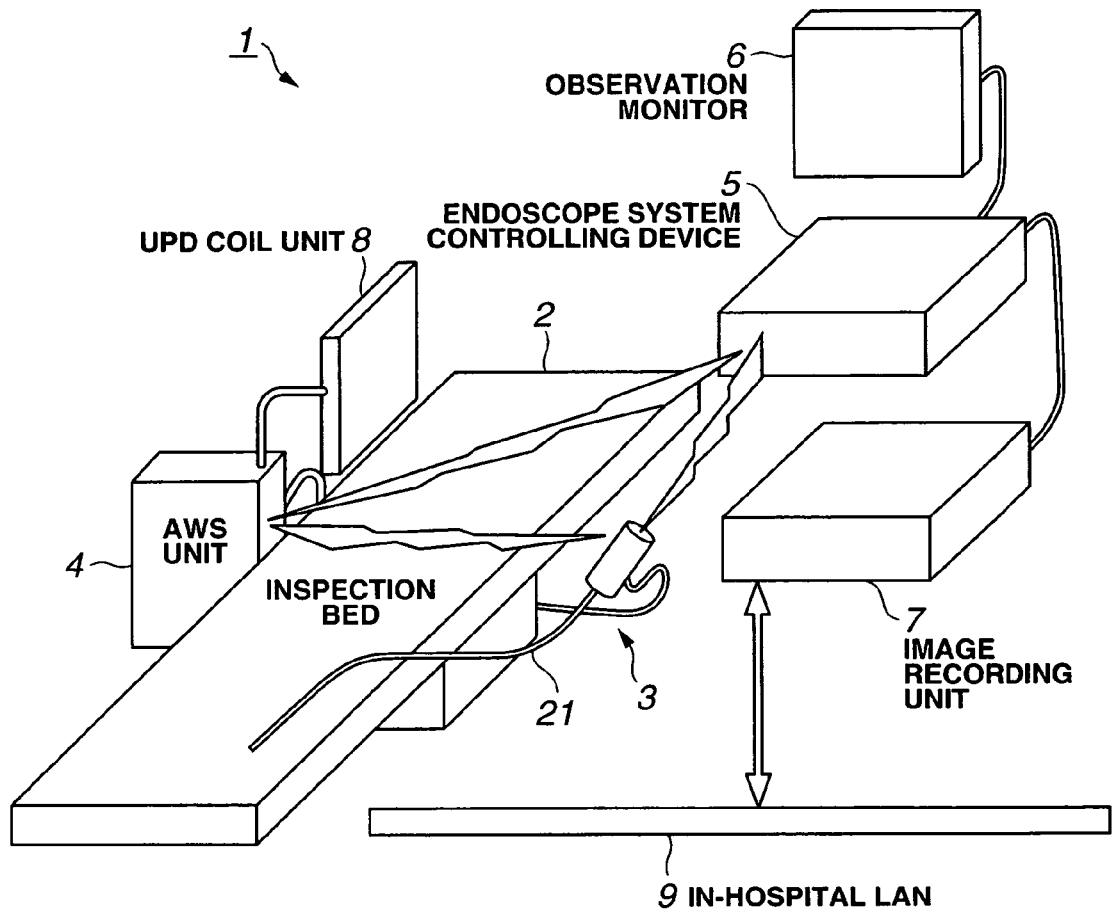
FIG. 1 is a schematic configuration diagram of an endoscope system applied with an endoscope of an embodiment of the present invention.
Figure 2A:
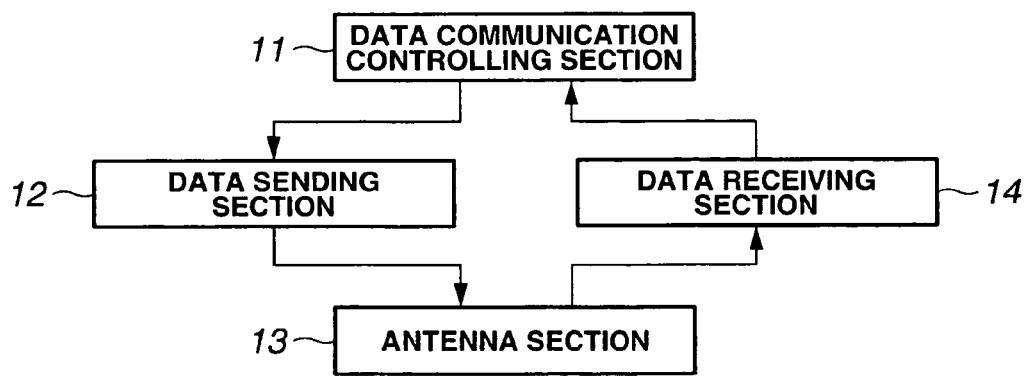
FIG. 2A is a diagram showing a form of data communication by a wireless method.
Figure 2B:
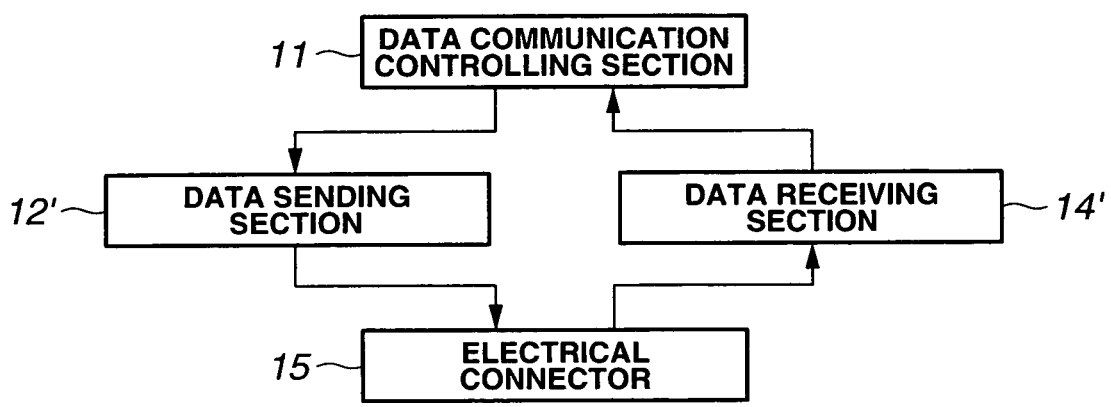
FIG. 2B is a diagram showing a form of data communication by a wired method.
Figure 2C:
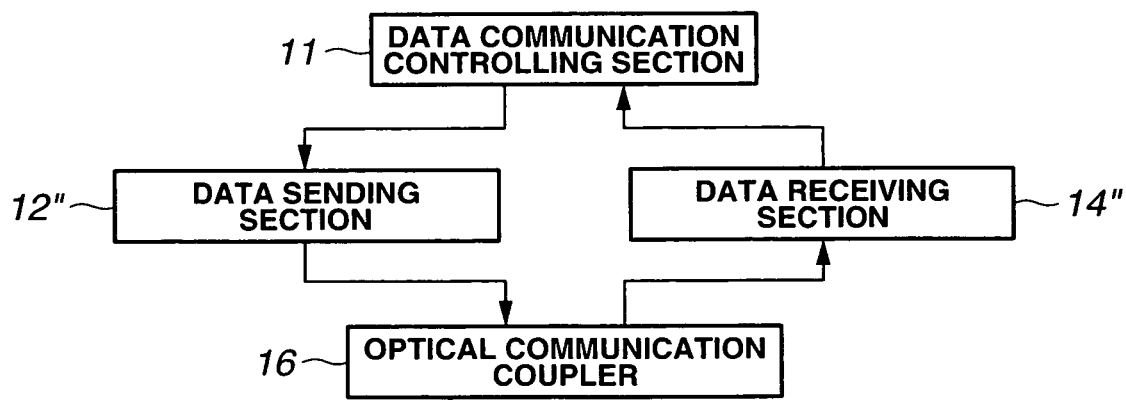
FIG. 2C is a diagram showing a form of data communication by an optical communication method.
Figure 3:
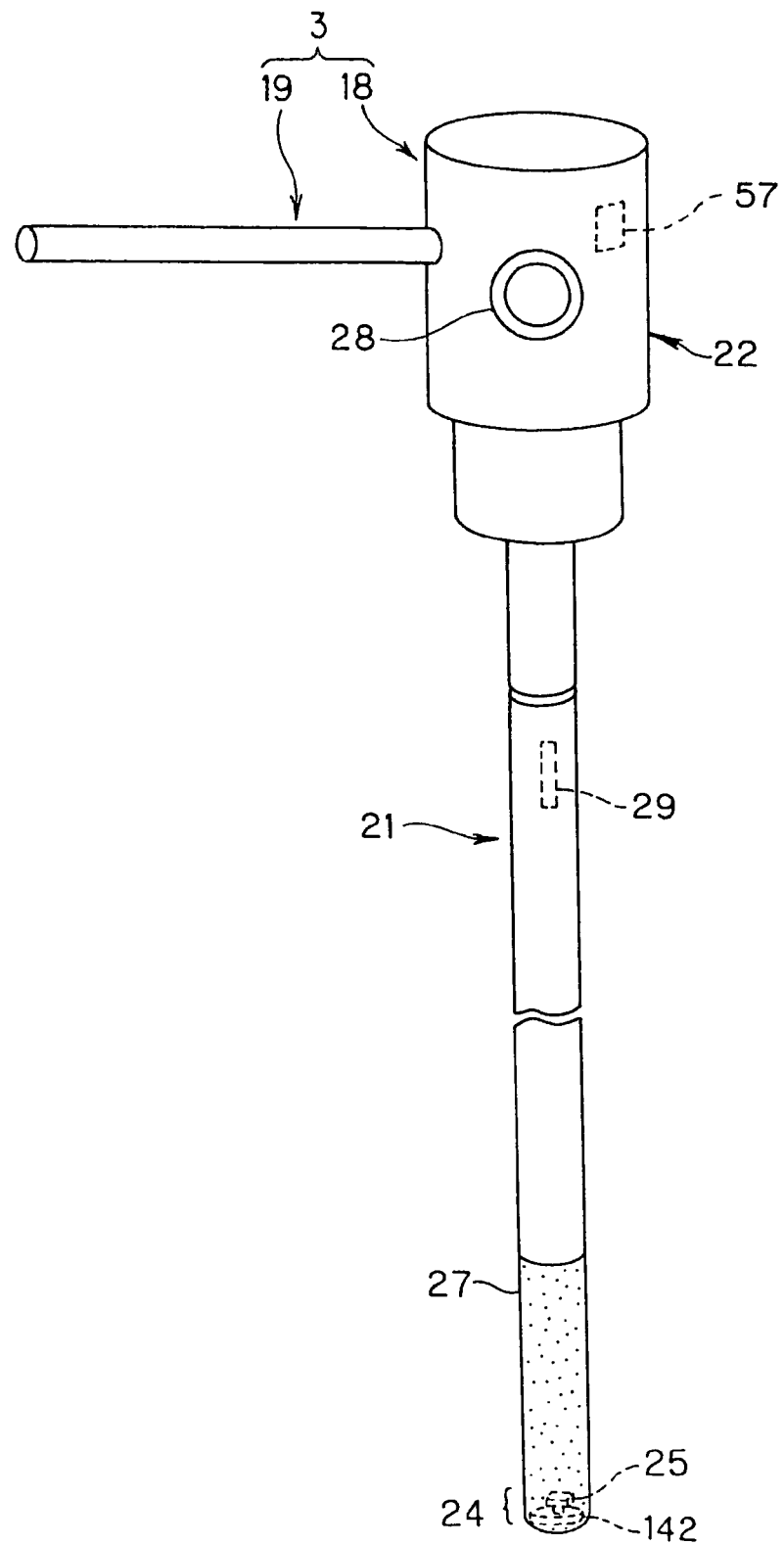
FIG. 3 is a diagram showing a schematic configuration of an endoscope in an embodiment of the present invention.
Figure 4:
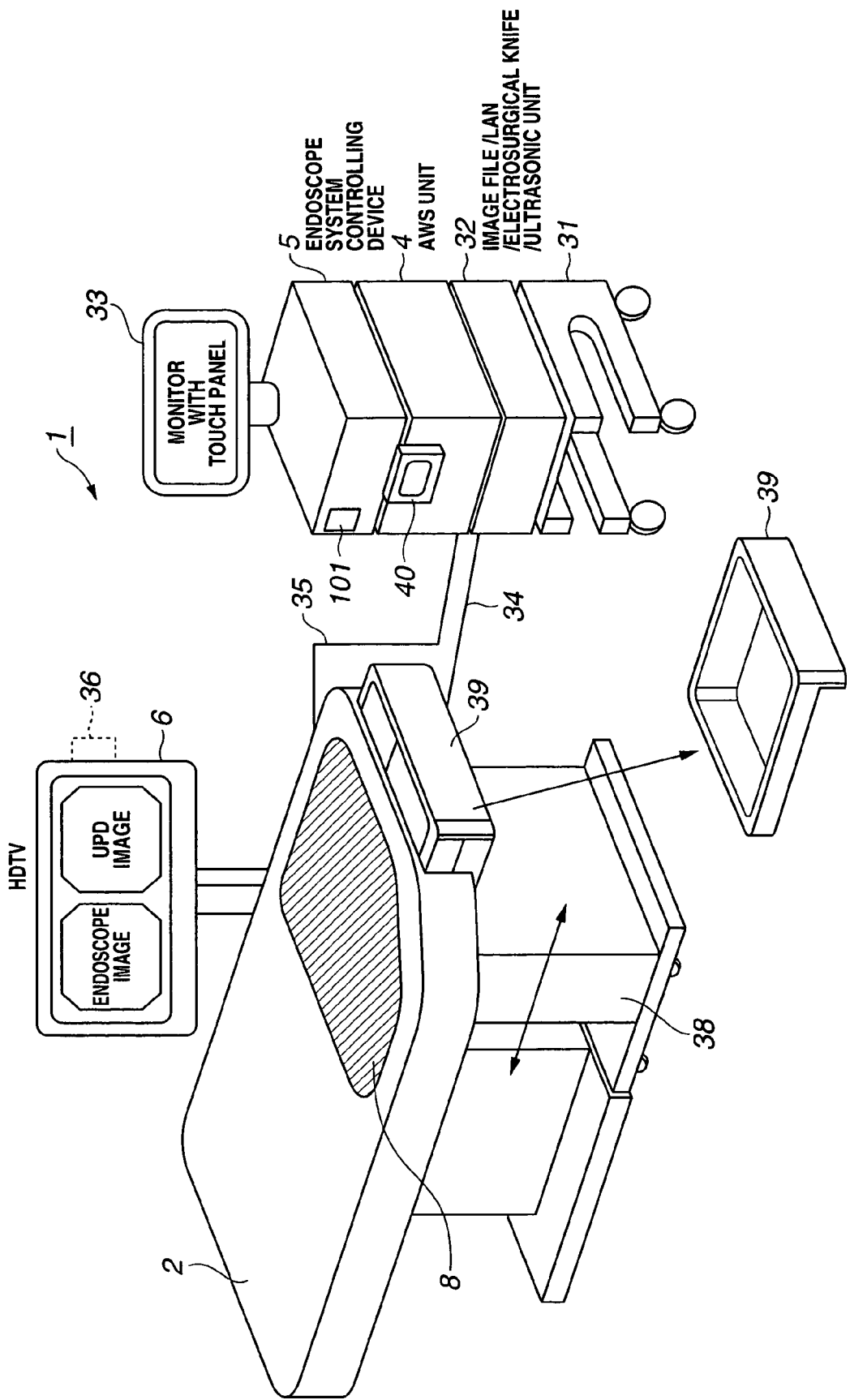
FIG. 4 is a perspective view showing an entire configuration of an endoscope system of the present embodiment.
Figure 5:
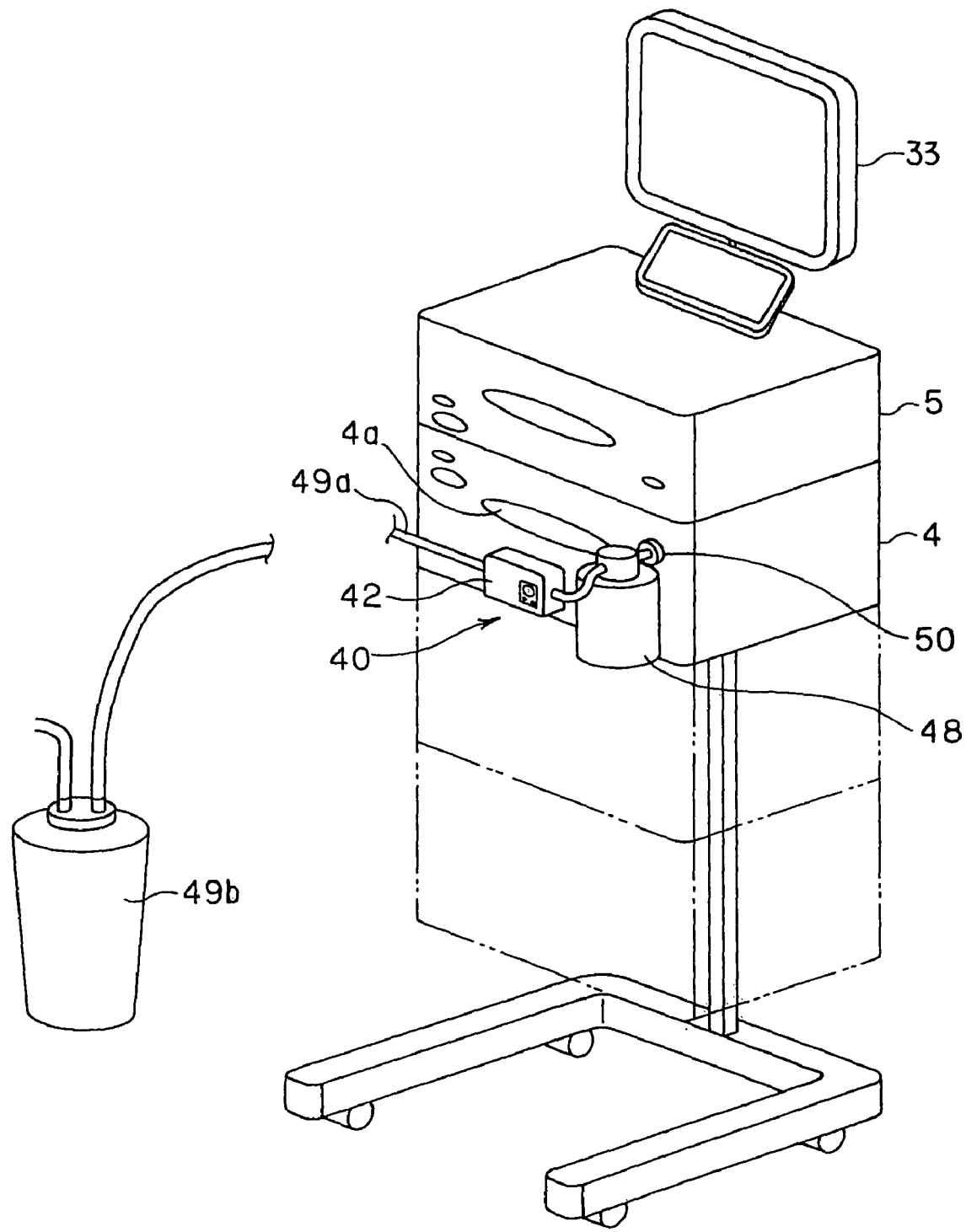
FIG. 5 is a perspective view showing a specific external shape of a periphery of an AWS unit.
Figure 6A:
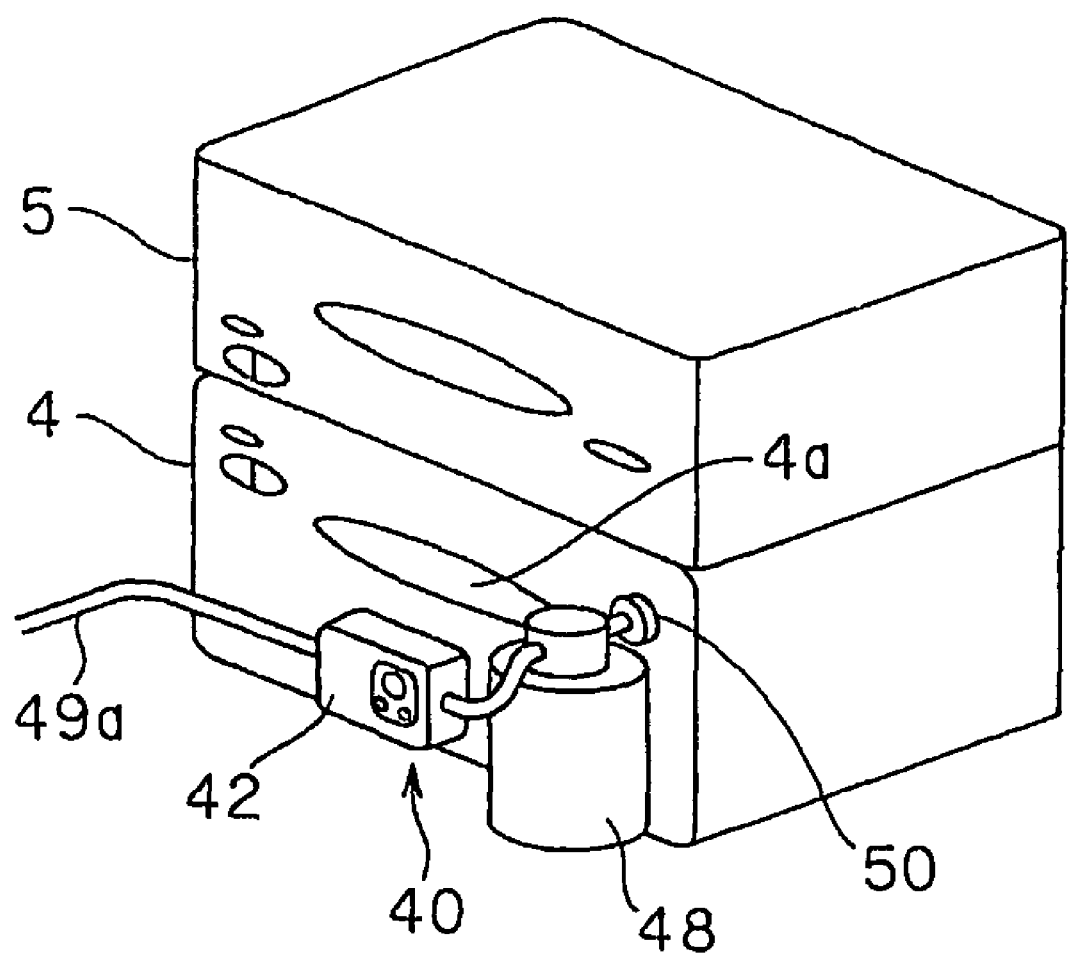
FIG. 6A is a diagram showing a status wherein the AWS unit is attached with a detachable AWS adaptor.
Figure 6B:
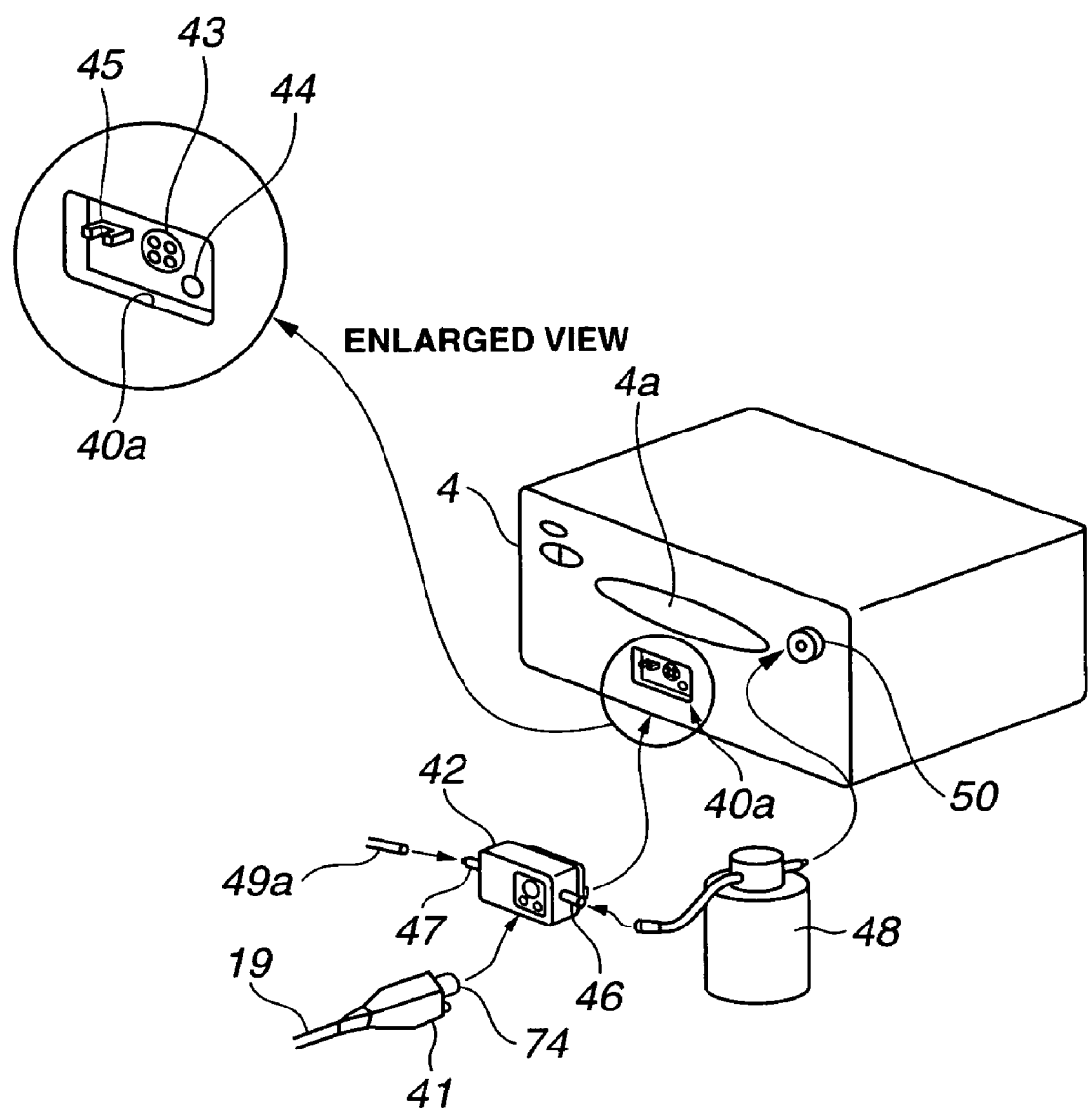
FIG. 6B is a diagram showing a status wherein the detachable AWS adaptor is detached from the AWS unit.
Figure 8:
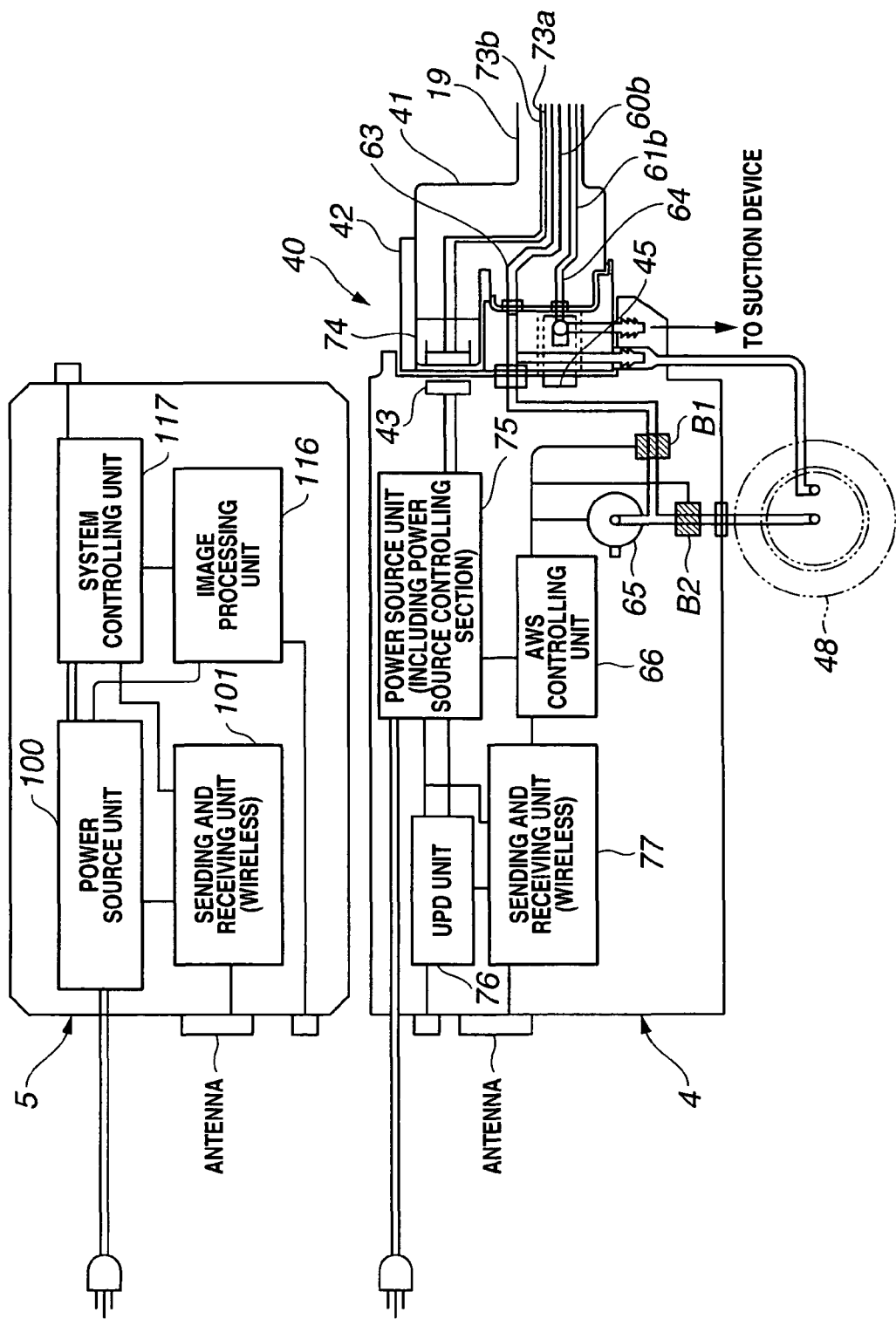
FIG. 8 is a diagram showing a structure of the AWS adaptor.
Figure 9:
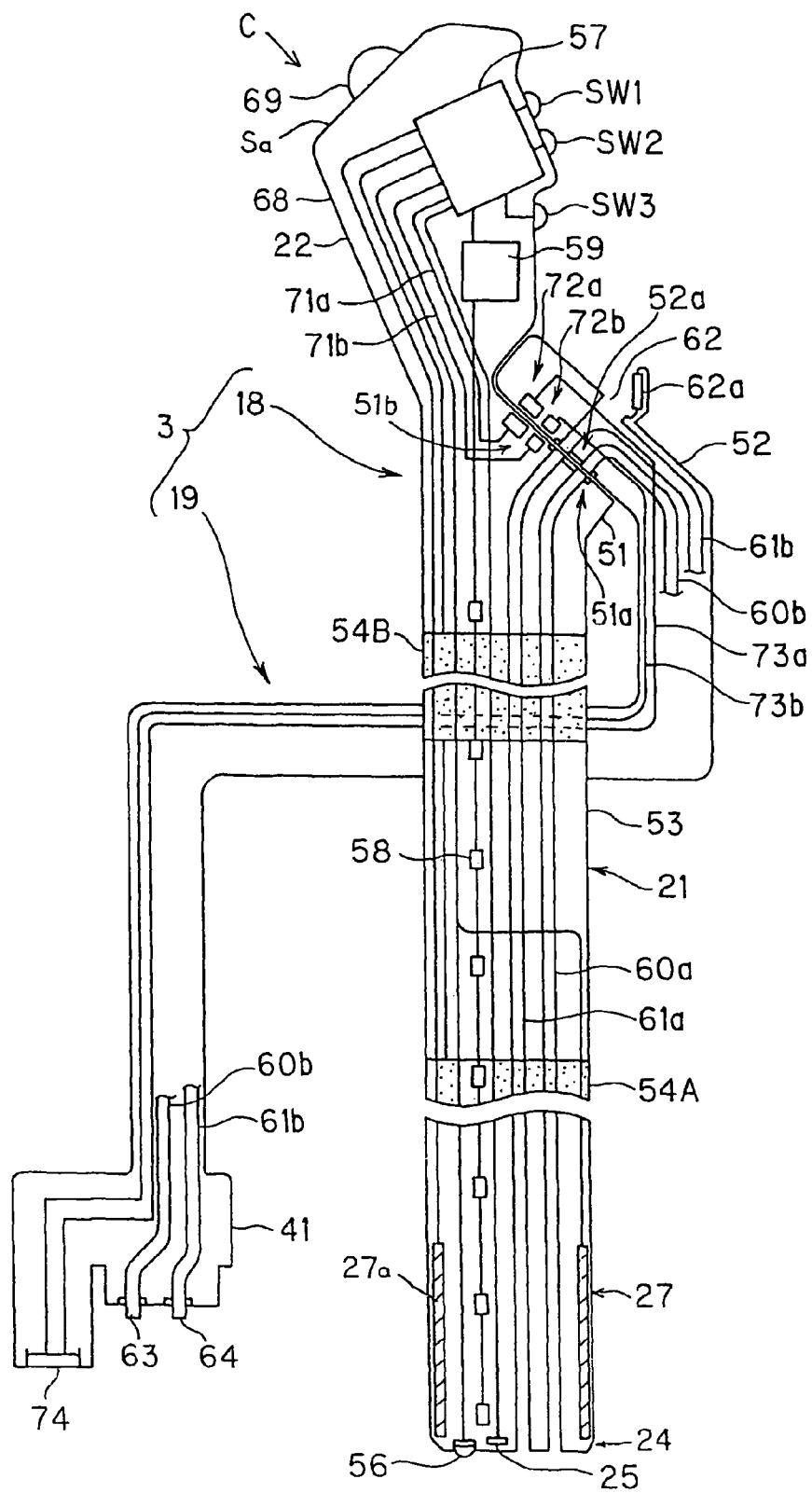
FIG. 9 is a side view transparently showing a part of inner components of the endoscope in an embodiment of the present invention.

FIGS. 1 to 25 relate to an embodiment of the present invention; FIG. 1 is a schematic configuration diagram of an endoscope system applied with an endoscope of an embodiment of the present invention; FIG. 2A is a diagram showing a form of data communication by a wireless method; FIG. 2B is a diagram showing a form of data communication by a wired method; FIG. 2C is a diagram showing a form of data communication by an optical communication method; FIG. 3 is a diagram showing a schematic configuration of an endoscope in an embodiment of the present invention; FIG. 4 is a perspective view showing an entire configuration of an endoscope system of the present embodiment; FIG. 5 is a view showing a specific external shape of a periphery of an AWS unit; FIG. 6A is a diagram showing a status the AWS unit is attached with a detachable AWS adaptor; FIG. 6B is a diagram showing a status wherein the detachable AWS adaptor is detached from the AWS unit; FIG. 7A is a front view of the AWS adaptor 42; FIG. 7B is a left side view of the AWS adaptor 42; FIG. 7C is a right side view of the AWS adaptor 42; FIG. 7D is a cross-sectional view taken along A-A' of FIG. 7A; FIG. 7E is a cross-sectional view taken along B-B' of FIG. 7A; FIG. 8 is a diagram showing an internal configuration of an endoscope system controlling device and the AWS unit; and FIG. 9 is a side view transparently showing a part of inner components of an endoscope in an embodiment of the present invention.

Figure 10A:
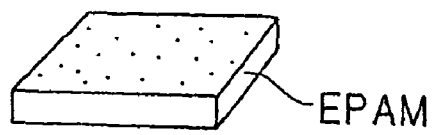
FIG. 10A is a diagram showing a schematic configuration of an Electropolymer Artificial Muscle (EPAM) used in an angle member and a variable rigidity actuator in the present embodiment.
Figure 10B:
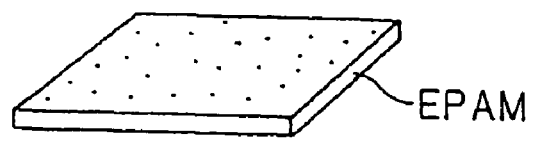
FIG. 10B is a diagram showing a status wherein the Electropolymer Artificial Muscle (EPAM) shown in FIG. 10A is shrunk in a thickness direction and extended in a longitudinal direction.
Figure 12:
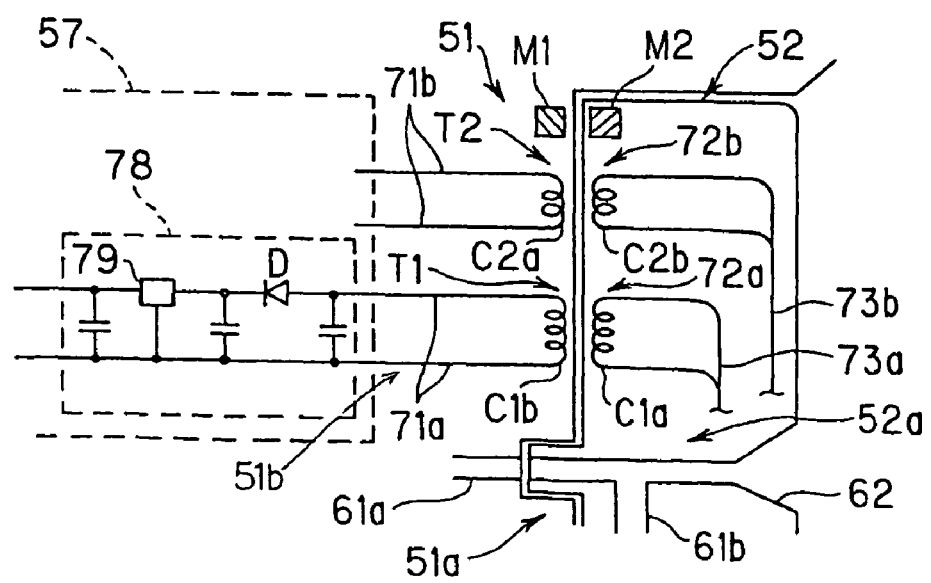
FIG. 12 is a circuit diagram showing a configuration of a contactless transmitting section in which a proximal end of a tube unit is contactlessly and detachably connected to the body of the operating section.
Figure 10C:
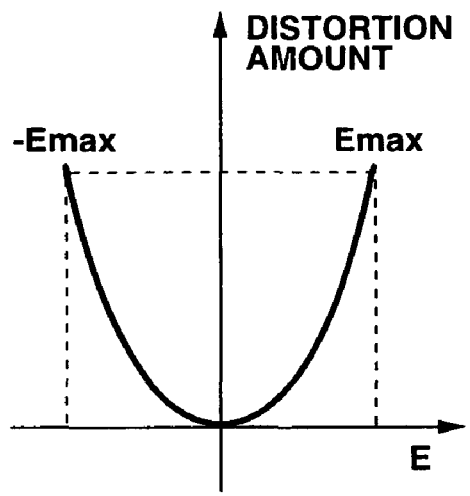
FIG. 10C is an illustrative diagram for showing an approximate distortion amount with respect to electric field strength due to an applied voltage, of the Electropolymer Artificial Muscle (EPAM) shown in FIG. 10A.
Figure 11:
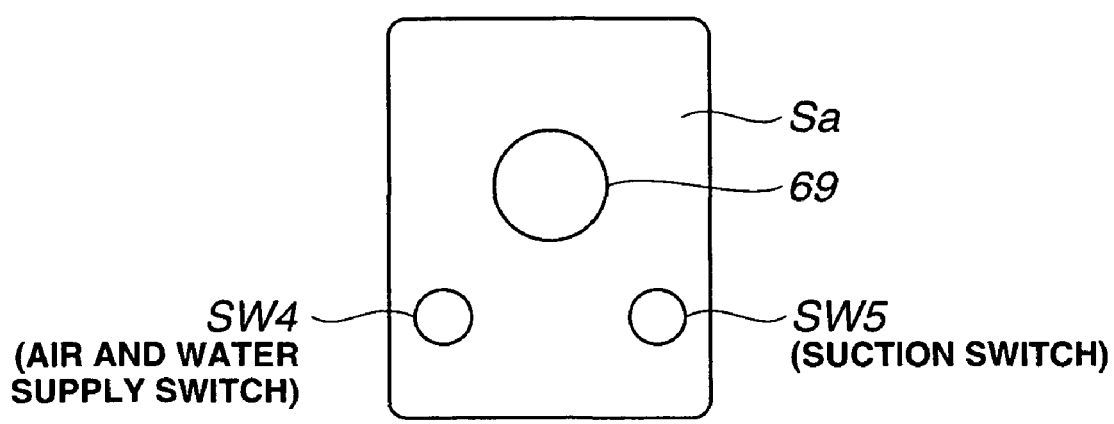
FIG. 11 is a diagram showing a track ball and the like provided to an operating section viewed in an arrow C in FIG. 9.
Figure 13:
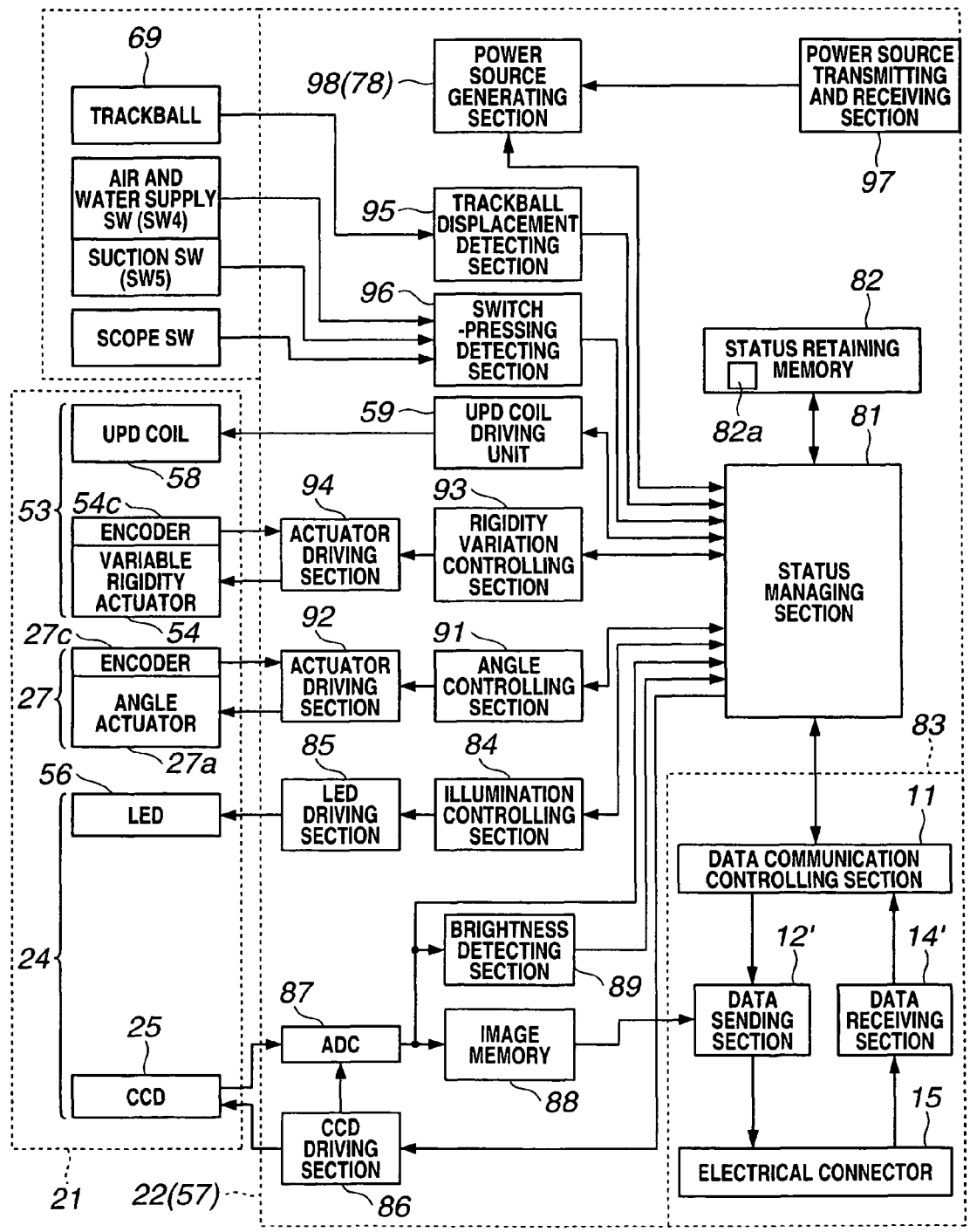
FIG. 13 is a block diagram showing a configuration of an electric system of components provided in the endoscope.
Figure 14:
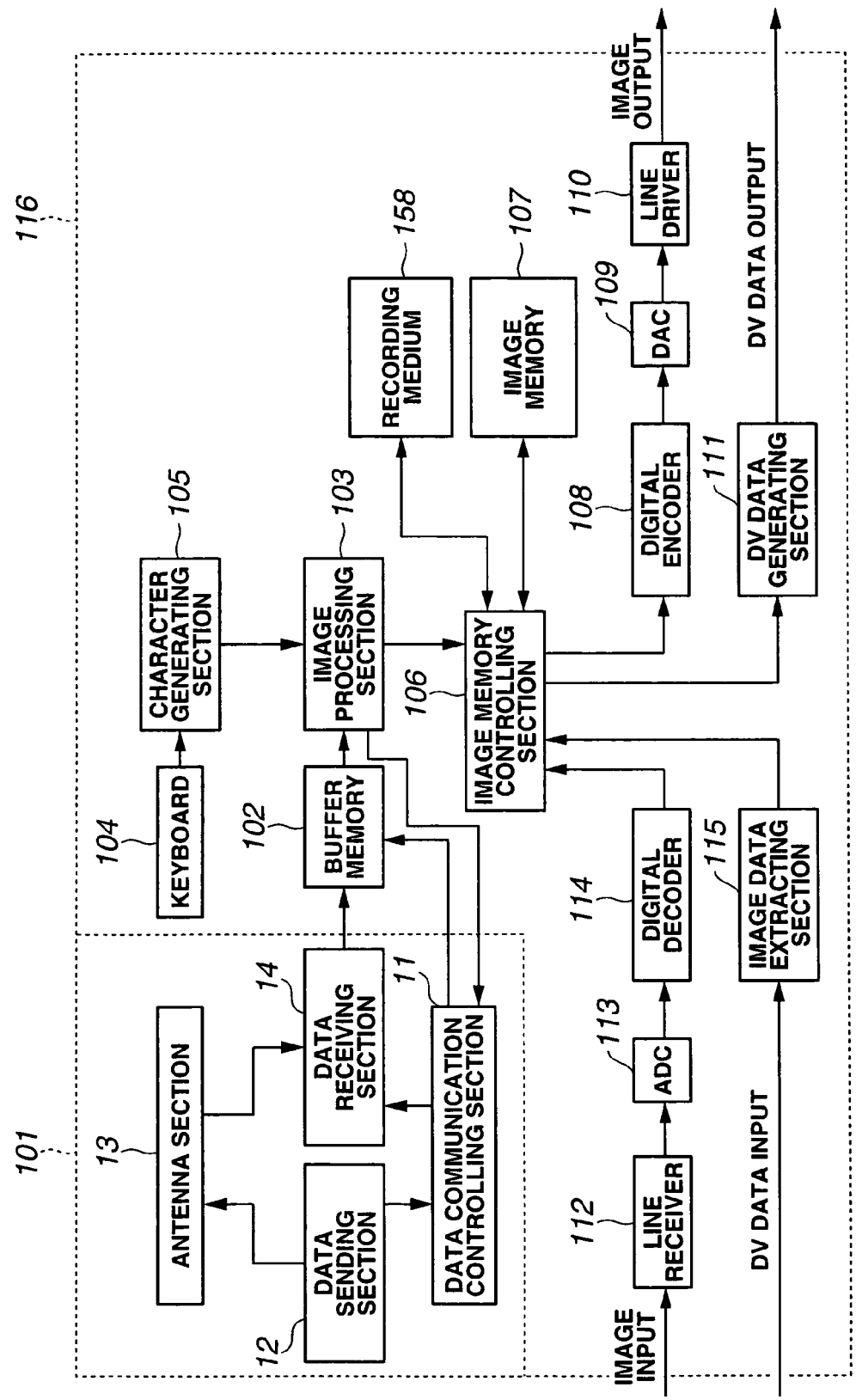
FIG. 14 is a block diagram showing a configuration of an electric system of a main portion of an endoscope system controlling device.
Figure 15:
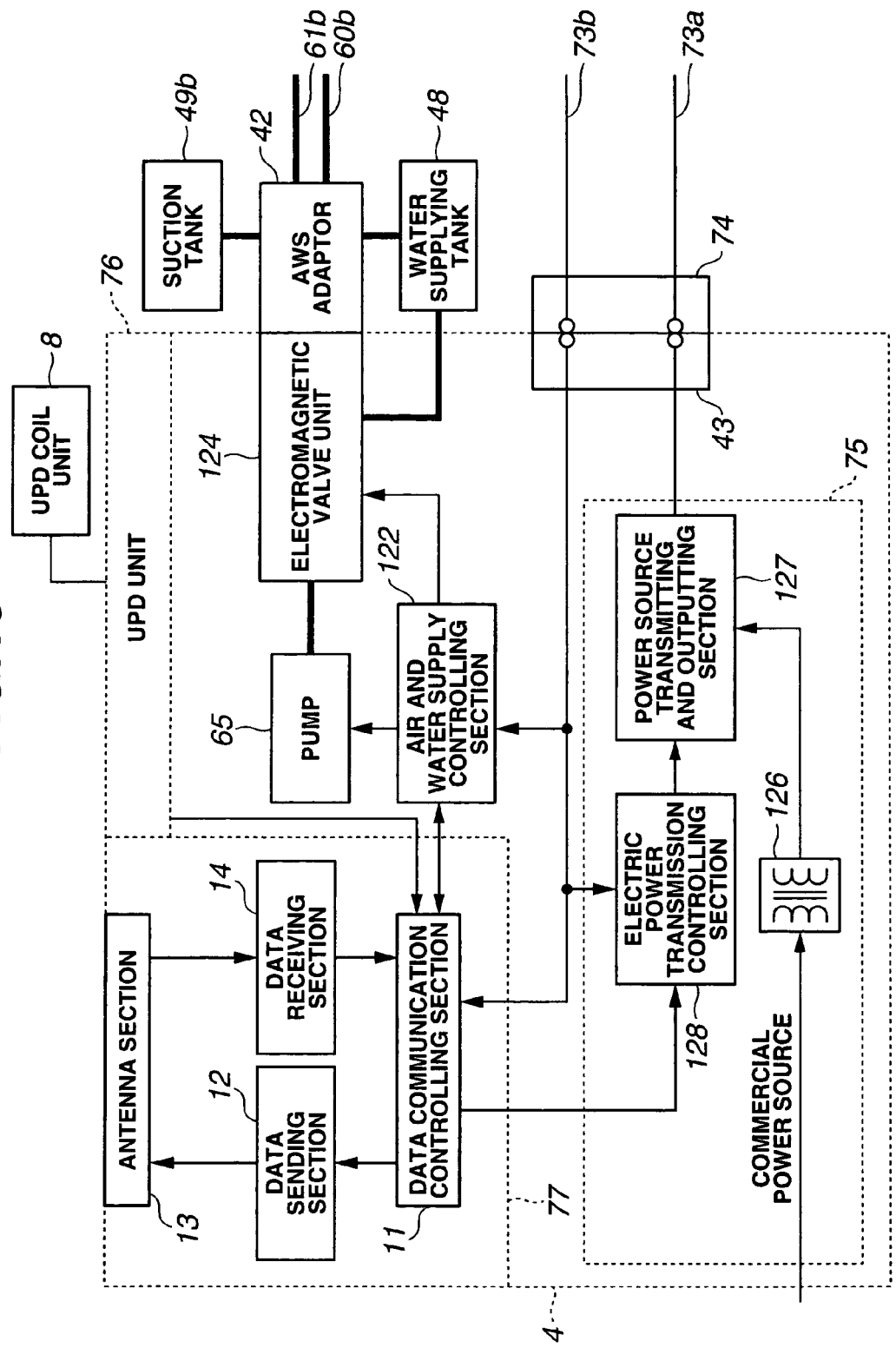
FIG. 15 is a block diagram showing a configuration of an electric system of the AWS unit.
Figure 16B:
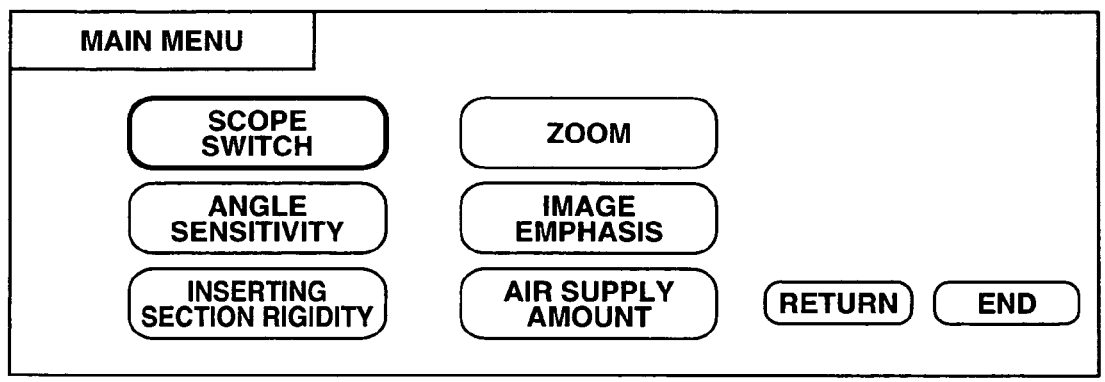
FIG. 16B is a diagram showing an example of an image of a main menu to be displayed in a menu displaying area of FIG. 16A.
Figure 16C:
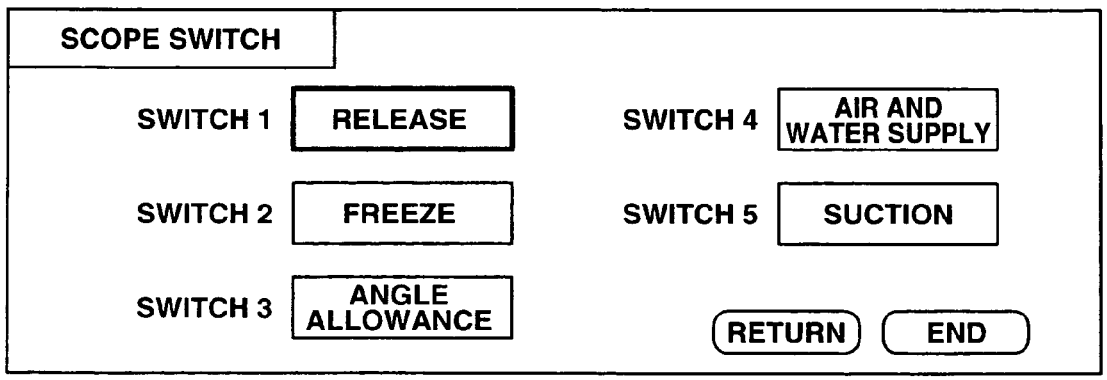
FIG. 16C is a diagram showing an example of an image of assigning scope switch functions, to be displayed in the menu displaying area of FIG. 16A.

Further, FIG. 10A is a diagram showing a schematic configuration of an Electropolymer Artificial Muscle (EPAM) used in an angle member and a variable rigidity actuator in the present embodiment; FIG. 10B is a diagram showing a status wherein the Electropolymer Artificial Muscle (EPAM) shown in FIG. 10A is shrunk in a thickness direction and extended in a longitudinal direction; FIG. 10C is an illustrative diagram for showing an approximate distortion amount with respect to electric field strength due to an applied voltage, of the Electropolymer Artificial Muscle (EPAM) shown in FIG. 10A; FIG. 11 is a diagram showing a track ball and the like provided to an operating section viewed in an arrow C in FIG. 9; FIG. 12 is a diagram showing a configuration of a contactless transmitting section in which a proximal end of a tube unit is contactlessly and detachably connected to the body of the operating section; FIG. 13 is a diagram showing a configuration of an electric system of components provided in the endoscope; FIG. 14 is a diagram showing a configuration of an electric system of a main portion of an endoscope system controlling device; FIG. 15 is a diagram showing a configuration of an electric system of the AWS unit; FIG. 16A is a diagram showing an example of an image to be displayed on a monitor right after the endoscope system is powered on; FIG. 16B is a diagram showing an example of an image of a main menu to be displayed in a menu displaying area of FIG. 16A; and FIG. 16C is a diagram showing an example of an image of assigning scope switch functions, to be displayed in the menu displaying area of FIG. 16A.

Figure 17:
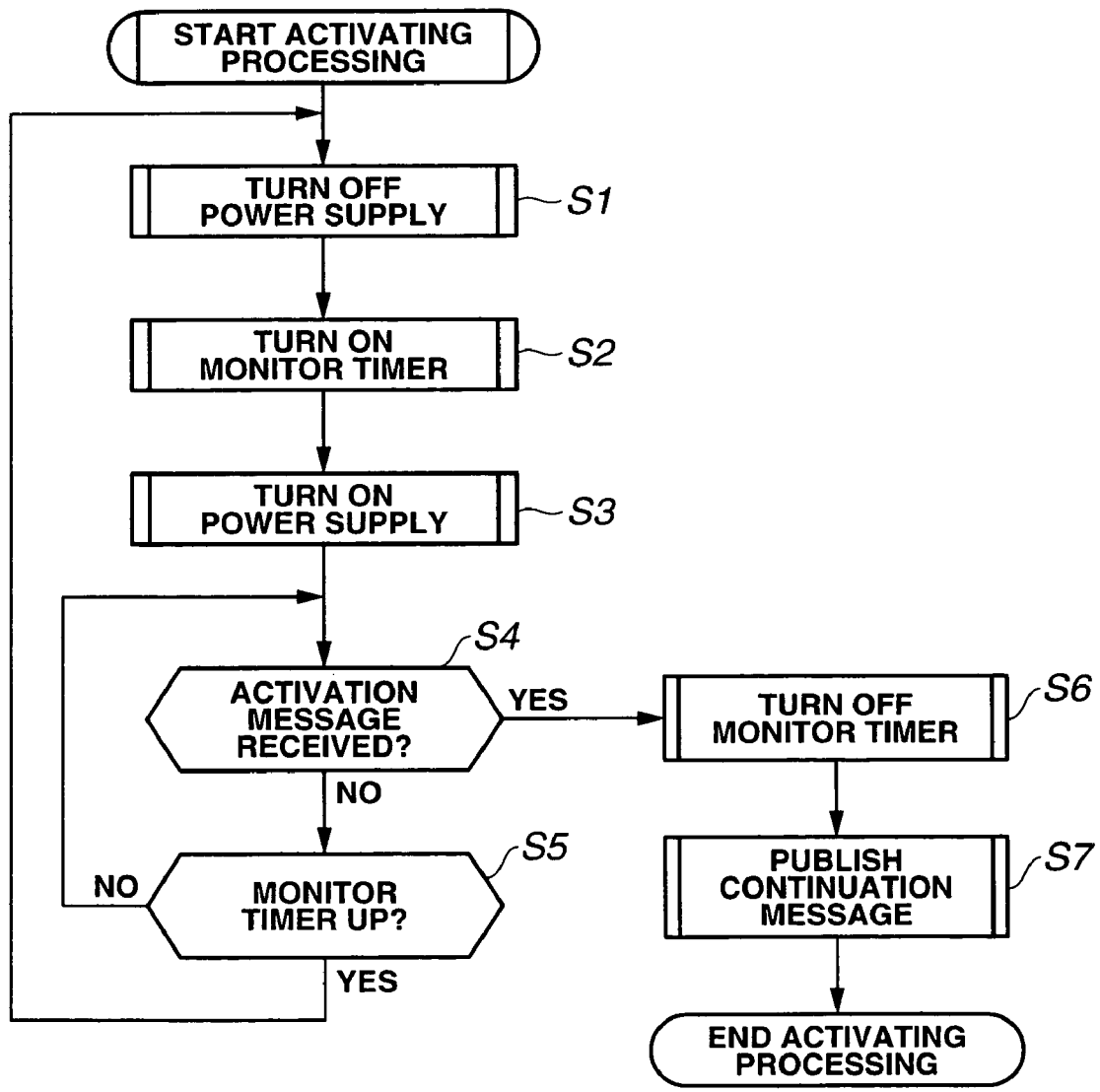
FIG. 17 is a flowchart diagram showing operational contents of an activating processing of the AWS unit.
Figure 18:
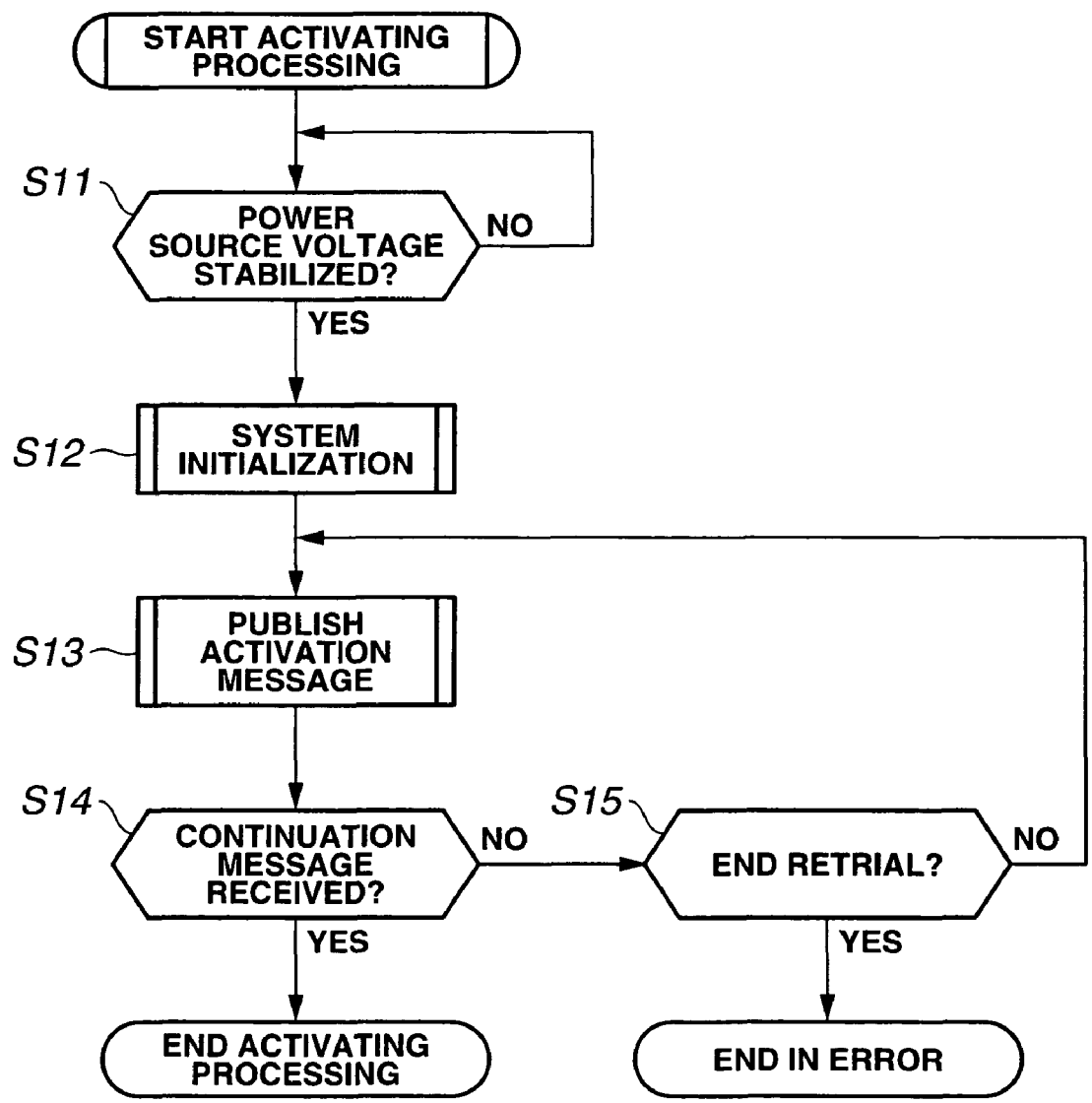
FIG. 18 is a flowchart diagram showing operational contents of an activating processing of the endoscope.
Figure 19:
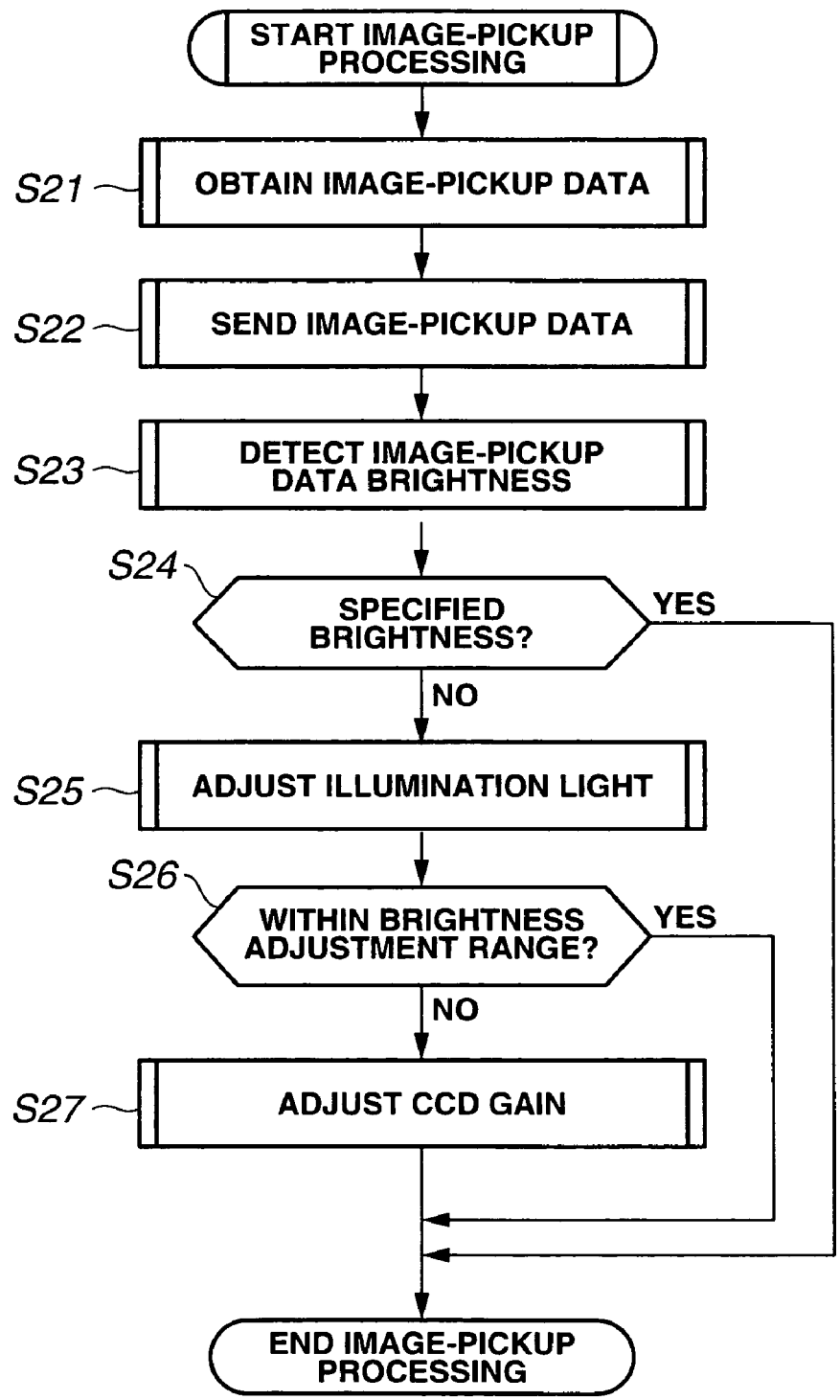
FIG. 19 is a flowchart diagram showing operational contents of an image-pickup control processing.
Figure 20:
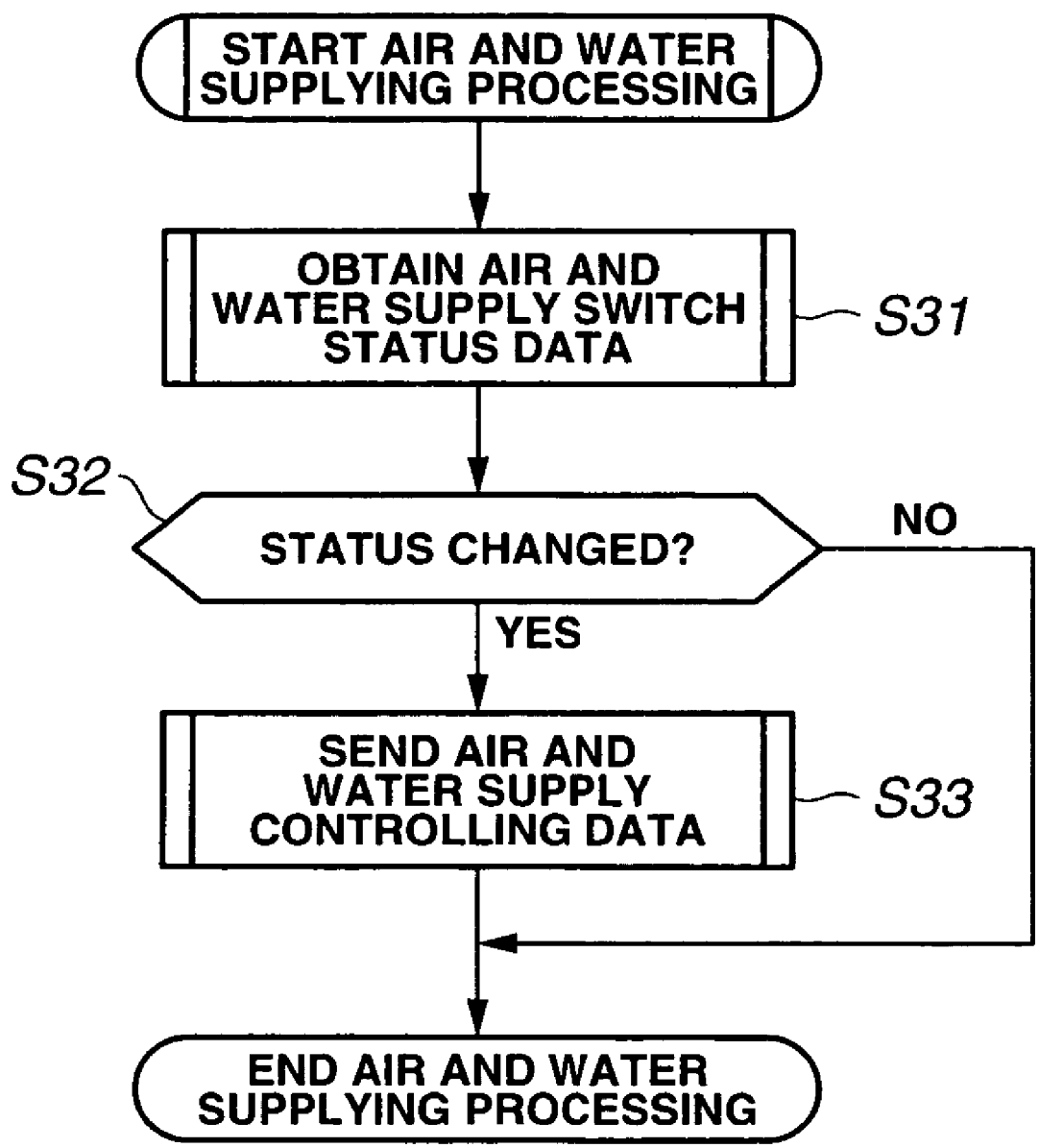
FIG. 20 is a flowchart diagram showing operational contents of an air and water supply control processing.
Figure 21:
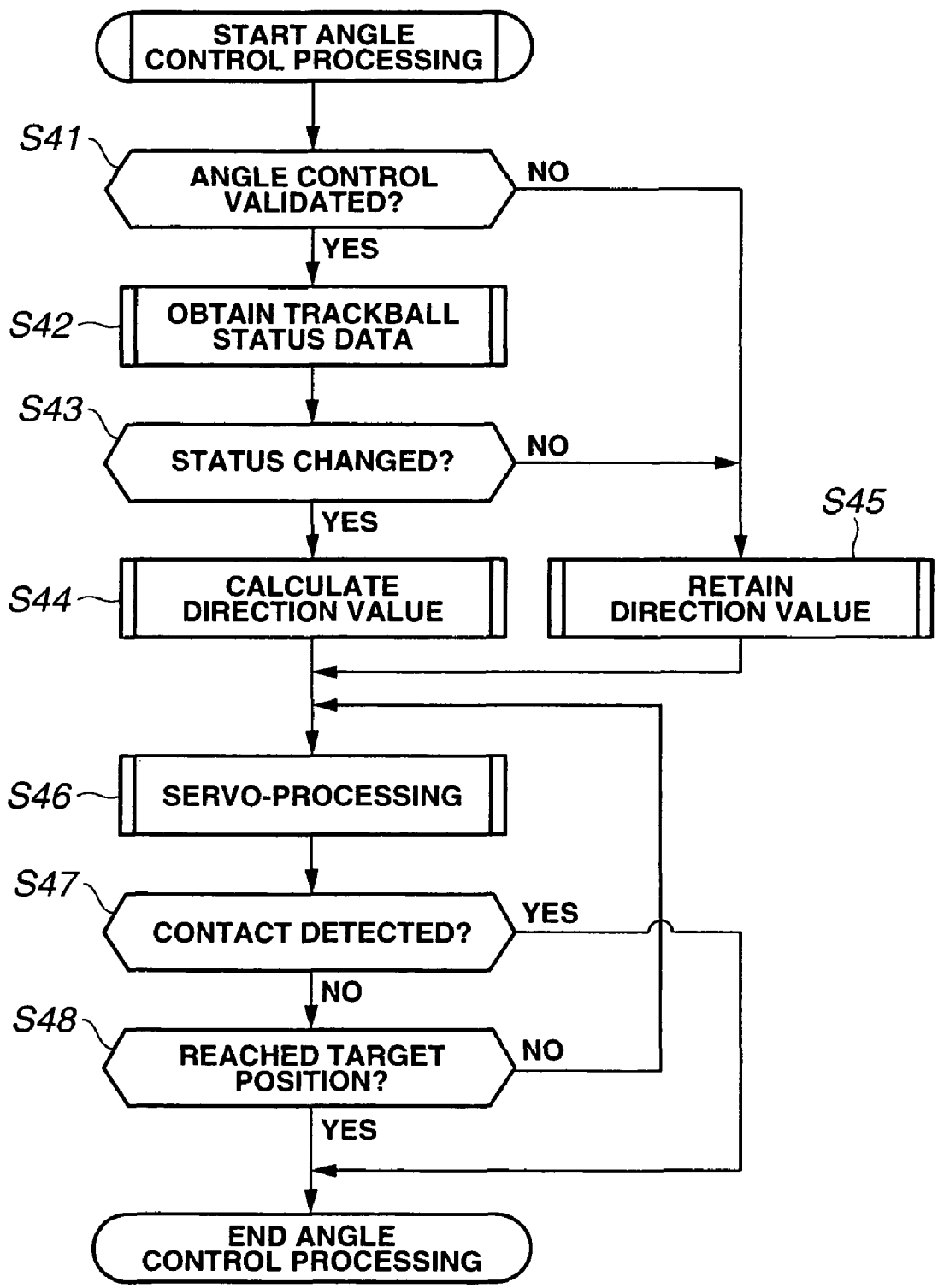
FIG. 21 is a flowchart diagram showing a control processing of an angle operation.
Figure 22:
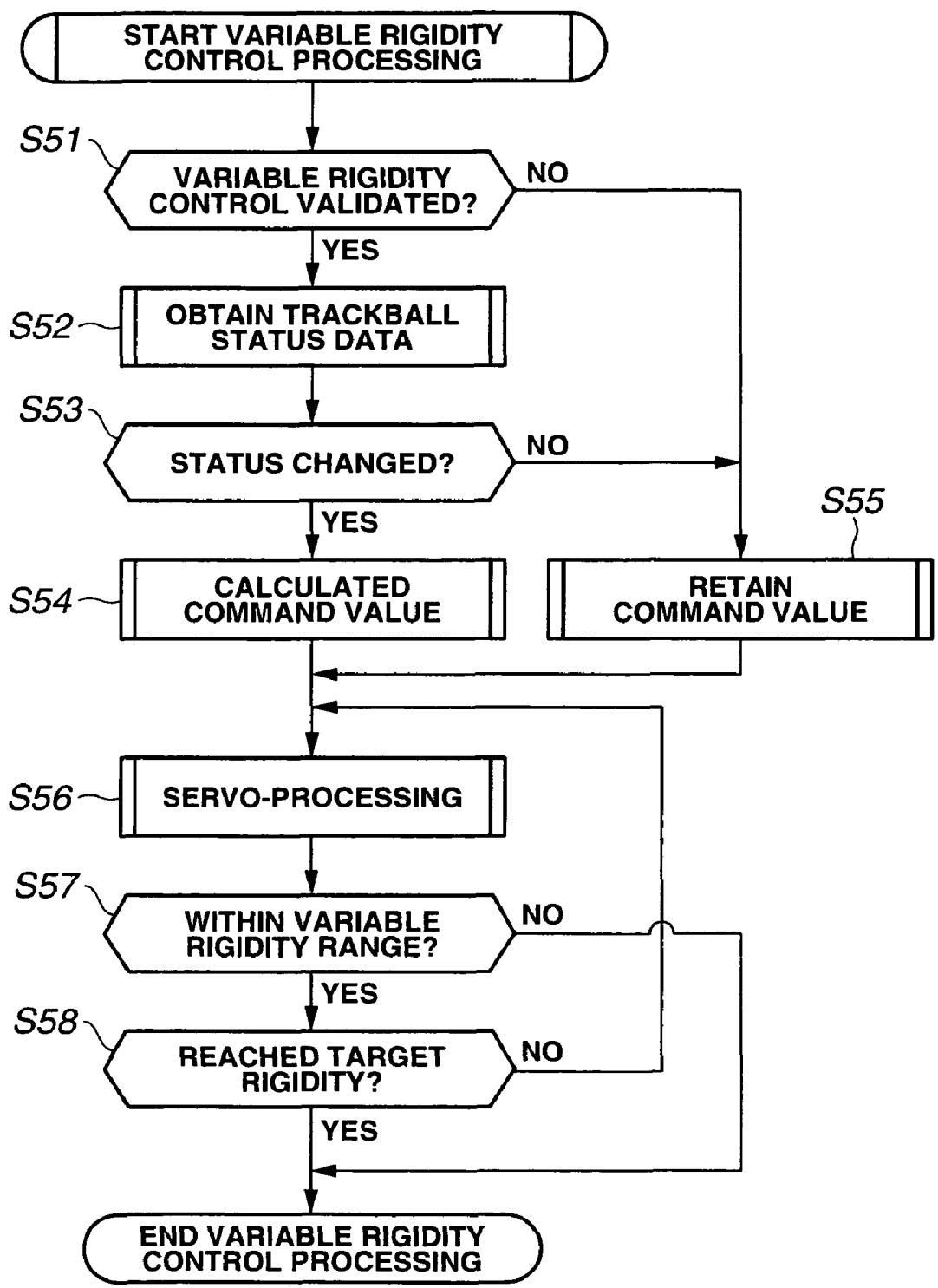
FIG. 22 is a flowchart diagram showing a controlling operation for a rigidity modifying operation.
Figure 23A:
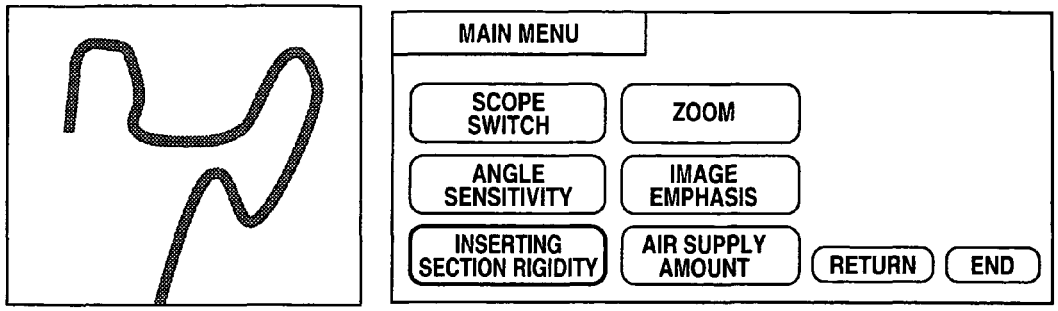
FIG. 23A is a diagram showing a display status of a main menu with a UPD image.
Figure 23B:
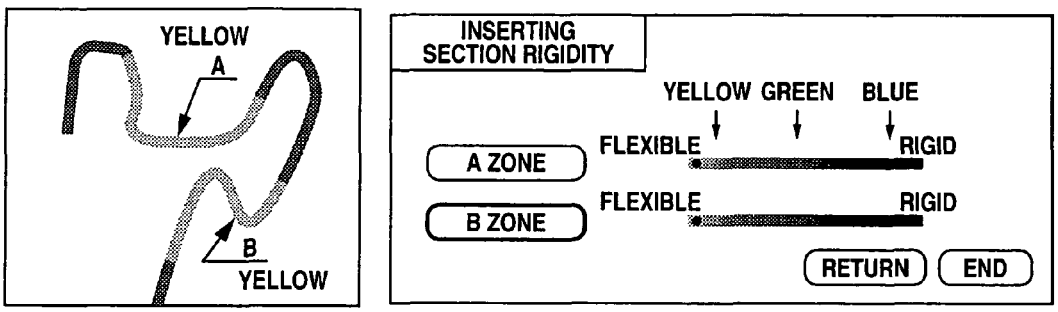
FIG. 23B is a diagram showing a display status of a rigidity setting screen with a UPD image.
Figure 23C:
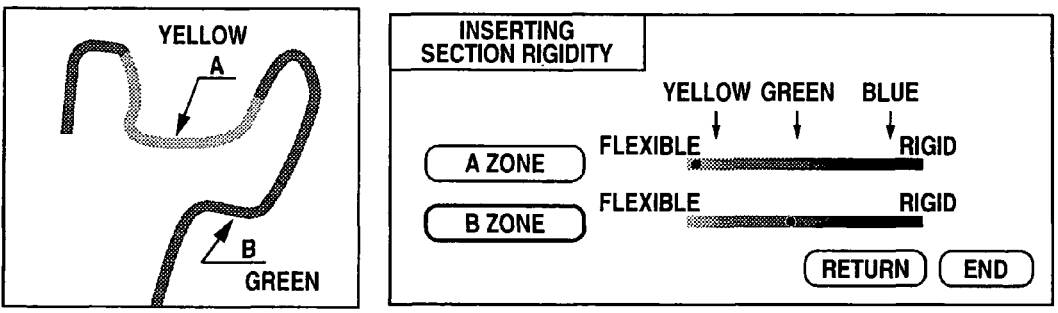
FIG. 23C is a diagram showing a display status of a rigidity setting screen with a UPD image, different from that of FIG. 23B.
Figure 23D:
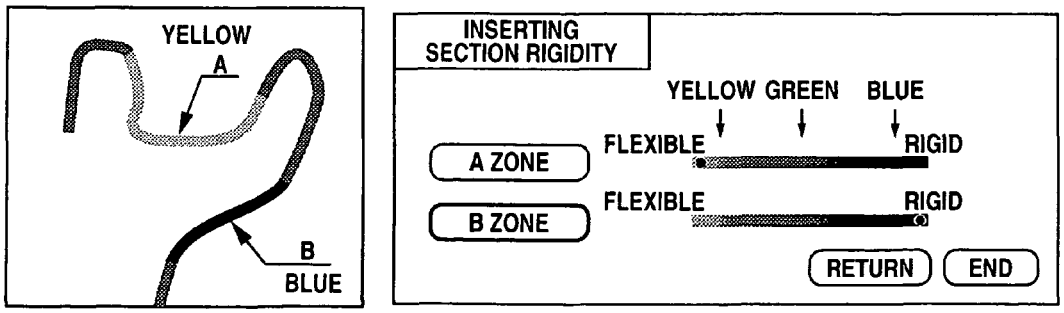
FIG. 23D is a diagram showing a display status of a rigidity setting screen with a UPD image, different from those of FIGS. 23B and 23C.
Figure 24:
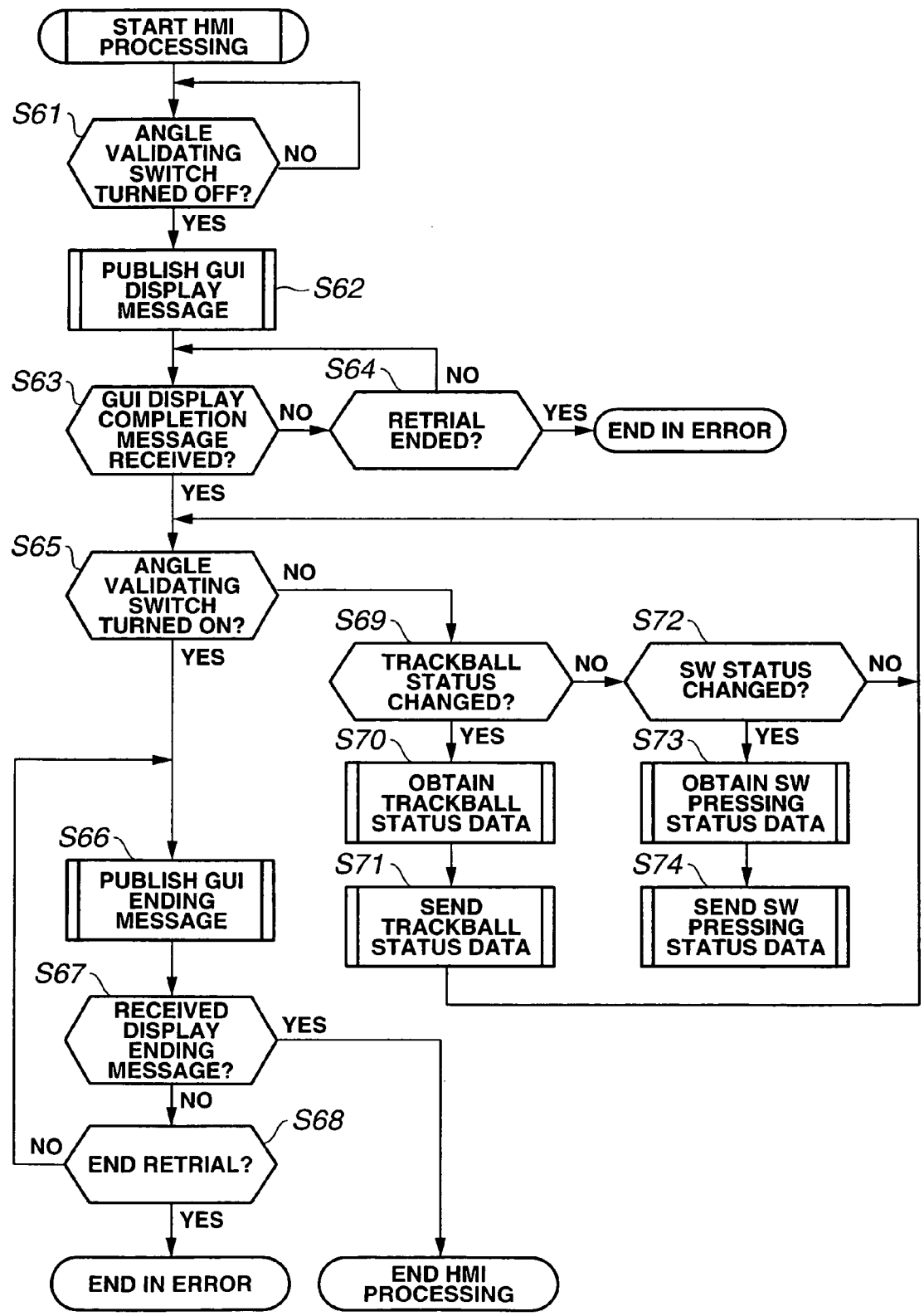
FIG. 24 is a flowchart diagram showing processing contents on the side of the endoscope in human interface.
Figure 25:
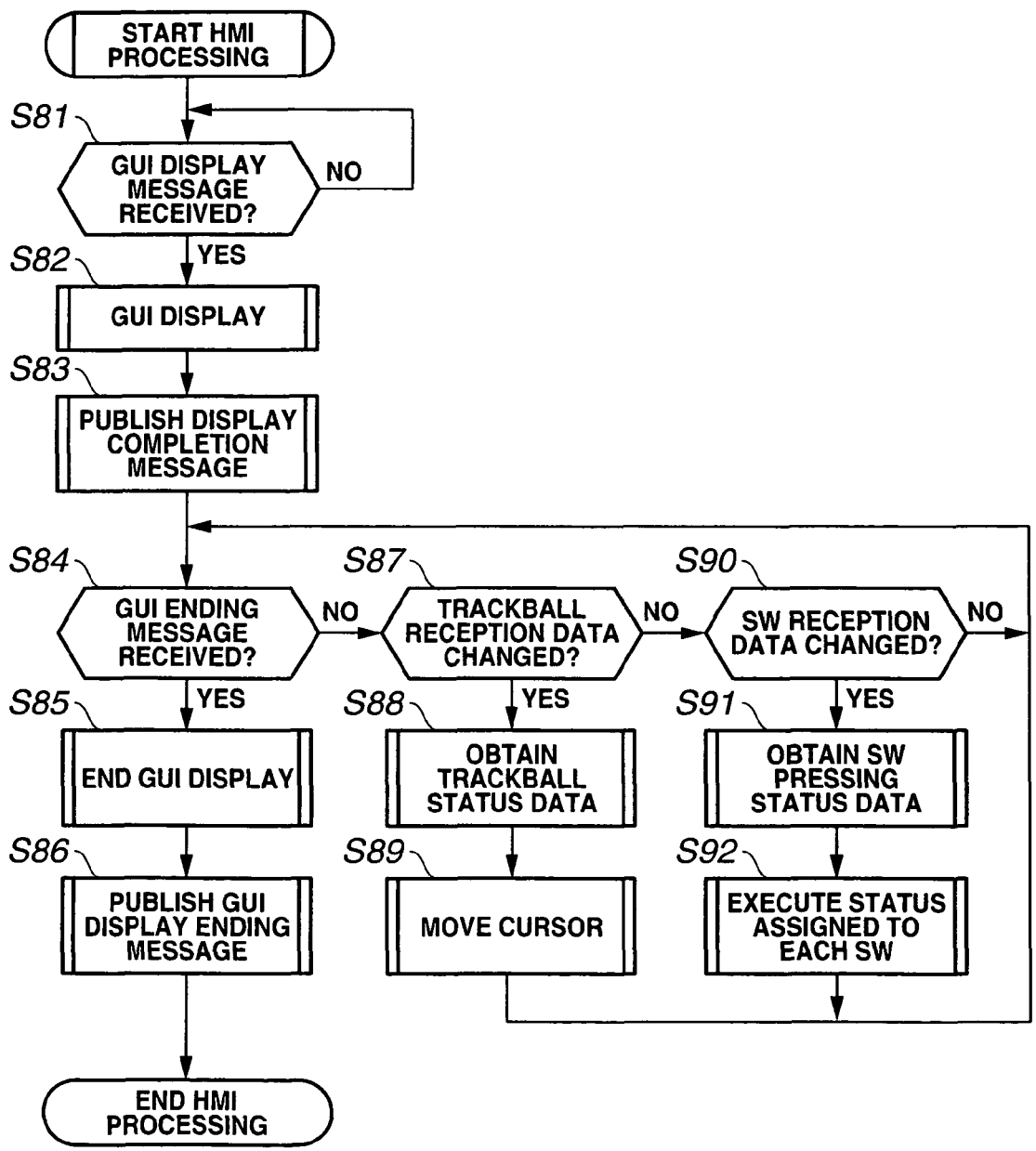
FIG. 25 is a flowchart diagram showing processing contents on the side of the endoscope system controlling device in human interface.

Furthermore, FIG. 17 is a flowchart diagram showing operational contents of an activating processing of the AWS unit; FIG. 18 is a diagram showing operational contents of an activating processing of the endoscope; FIG. 19 is a diagram showing operational contents of an image-pickup control processing; FIG. 20 is a diagram showing operational contents of an air and water supply control processing; FIG. 21 is a diagram showing a control processing of an angle operation; FIG. 22 is a diagram showing a controlling operation for a rigidity modifying operation; FIG. 23A is a diagram showing a display status of a main menu with a UPD image; FIG. 23B is a diagram showing a display status of a rigidity setting screen with a UPD image; FIG. 23C is a diagram showing a display status of a rigidity setting screen with a UPD image, different from that of FIG. 23B; FIG. 23D is a diagram showing a display status of a rigidity setting screen with a UPD image, different from those of FIGS. 23B and 23C; FIG. 24 is a flowchart diagram showing processing contents on the side of the endoscope in human interface; and FIG. 25 is a flowchart diagram showing processing contents on the side of the endoscope system controlling device in human interface.

Before describing a specific configuration of the present invention, a schematic configuration of the present invention will be described referring to FIGS. 1 to 3.

As shown in FIG. 1, an endoscope system 1 comprising the present invention comprises: a flexible endoscope (also referred to as scope) 3 for performing endoscopy, which is inserted into a body cavity of a patient not shown lying on an inspection bed 2; an air and water supplying and sucking unit (hereinafter abbreviated as AWS unit) 4 connected with the endoscope 3 and having air and water supplying and sucking functions; an endoscope system controlling device 5 for performing signal processing for an image-pickup element incorporated in the endoscope 3, control processing for various inputting sections provided in the endoscope 3, and so on; and an observation monitor 6 of a liquid crystal monitor and the like for displaying an image signal generated by the endoscope system controlling device 5.

The endoscope system 1 also comprises: an image recording unit 7 for performing filing and the like of, for example, a digital image signal generated by the endoscope system controlling device 5; and a UPD coil unit 8 which is connected to the AWS unit 4, and which, when the inserting section of the endoscope 3 incorporates shape detecting coils (hereinafter abbreviated as "UPD coils"), detects the position of each of the UPD coils by, for example, receiving an electromagnetic field signal generated by the UPD coil to display the shape of the inserting section of the endoscope 3.

The image recording unit 7 is connected to an in-hospital LAN 9 provided with the endoscope system 1, so that a user can refer to images and the like filed in the image recording unit 7 by using each terminal device wiredly or wirelessly connected to the LAN 9.

As shown in FIG. 1, the AWS unit 4 and the endoscope system controlling device 5 are configured to wirelessly send and receive information (data). It is to be noted that the endoscope 3, although connected to the AWS unit 4 with a cable in FIG. 1, may wirelessly send and receive (bi-directionally transmit) information (data). Moreover, the endoscope system controlling device 5 may wirelessly send and receive information to and from the endoscope 3.

FIGS. 2A to 2C show three methods in a sending and receiving unit (communication section) for sending and receiving data between a unit and a device, between the endoscope 3 and a unit, or between devices in the endoscope system 1. FIG. 2A describes, as a specific example, a case with the AWS unit 4 and the endoscope system controlling device 5.

FIG. 2A shows a wireless method wherein a data communication controlling section 11 incorporated in the AWS unit 4 modulates data through a data sending section 12, and wirelessly sends the data from an antenna section 13 to the endoscope system controlling device 5.

The AWS unit 4 receives with the antenna section 13 the data wirelessly sent from the endoscope system controlling device 5, and then with a data receiving section 14 demodulates and sends the data to the data communication controlling section 11. In the present invention, for sending data by the wireless method, a wireless LAN with a maximum data transmission speed of 54 Mbps is formed with, for example, the IEEE802.11g standard.

FIG. 2B is a wired method, and describes as a specific example a case in which data is sent and received between the endoscope 3 and the AWS unit 4. The data communication controlling section 11 incorporated in the endoscope 3 wiredly sends data from an electrical connector 15 to the AWS unit 4 through a data sending section 12'. Data sent from the AWS unit 4 to the endoscope 3 is transmitted through the electrical connector 15 and a data receiving section 14' to the data communication controlling section 11.

FIG. 2C shows an optical communication method, and describes as a specific example a case in which data is sent and received between the AWS unit 4 and the endoscope system controlling device 5. The data communication controlling section 11 incorporated in the endoscope 3 is connected to an optical communication coupler 16 provided to the AWS unit 4, via a data sending section 12" and a data receiving section 14" for sending and receiving data for optical communication, to send and receive data via an optical communication coupler on the side of the endoscope system controlling device 5.

FIG. 3 shows a schematic configuration of the endoscope 3 of the present invention. The endoscope 3 comprises an endoscope body 18, and a tube unit 19 which is detachably connected to the endoscope body 18 and is, for example, a disposable type. The tube unit 19 has a diameter smaller than that of a conventional universal cable, and in the present embodiment, only comprises two channel tubes 63, 64, a power source line 73a, and a signal line 73b.

The endoscope body 18 comprises a flexible inserting section 21 to be inserted into a body cavity, and an operating section 22 provided at a rear end of the inserting section 21. To the operating section 22, a proximal end of the tube unit 19 is detachably connected.

To a tip end portion 24 of the inserting section 21 is placed as an image-pickup element an image-pickup unit using a CCD 25 capable of varying gain in the image-pickup element. To the tip end portion 24 is also provided a contact sensor 142 for detecting a status wherein the tip end portion 24 is in (pressed) contact with an intracavital inner wall and the like To a rear end of the tip end portion 24, a bending portion 27 which can be bent with a small amount of force is provided. The bending portion 27 can be bent by operating an angle and remote-control manipulator 28 provided to the operating section 22. The angle and remote-control manipulator 28 can perform angle (bending) operation, operations of air and water supplying and sucking and so on, and remote control operation for the endoscope system controlling device 5 and the like (specifically, freeze directing and release directing operations), and so forth. To the inserting section 21, a variable rigidity portion is formed, allowing for smooth insertion and the like.

In addition, in the inserting section 21, a cleaning level detecting portion 29 is provided, so that a cleaning level and the like of the channel can be detected.

Next, referring to FIG. 4, a more specific configuration of the endoscope system 1 will be described.

Adjacent to a side of the inspection bed 2, an observing monitor 6 comprising a liquid crystal monitor and the like is placed. On a cart 31 movably placed near one end in a longitudinal direction of the inspection bed 2 are placed: the endoscope system controlling device 5; the AWS unit 4; an image file/LAN/electrosurgical knife/ultrasonic unit (simplified denotation of an image file unit, a wireless or wired LAN, an electrosurgical knife device, an ultrasonic unit, and so on) 32; and on top thereof, a monitor with a touch panel 33.

In an upper surface portion of the inspection bed 2 on which a patient lies, the UPD coil unit 8 serving as an endoscope shape detecting section is embedded. The UPD coil unit 8 is connected to the AWS unit 4 with a UPD cable 34.

In the present embodiment, the AWS unit 4 and the endoscope system controlling device 5 send and receive data to and from each other by wireless sending and receiving units 77, 101, as shown in FIG. 8, for example. The observation monitor 6 serving as a display section is connected to a monitor connector of the endoscope system controlling device 5, with a monitor cable 35, as shown in FIG. 4.

It should be noted that as shown in FIG. 4, the endoscope system controlling device 5 and the observation monitor 6 may be attached with the sending and receiving unit 101 and a sending and receiving unit 36, respectively, to send picture signals from the endoscope system controlling device 5 to the observation monitor 6, so as to allow for displaying on a screen thereof an endoscope image corresponding to each of the picture signals.

As will be described later, to the endoscope system controlling device 5 are sent image data of the shape of the inserting section of the endoscope 3 (UPD image) detected by using the UPD coil unit 8, along with image data picked up by the CCD 25 from the side of the AWS unit 4. Thus, the endoscope system controlling device 5 sends image signals corresponding to these image data to the observation monitor 6, so that the UPD image can also be displayed on the screen thereof along with an endoscope image.

The observation monitor 6 is configured with a monitor of a high-definition TV (HDTV) so that a plurality of kinds of images can thus be displayed on the screen thereof at the same time.

Also, in this embodiment, at a position at the one end in the longitudinal direction of the inspection bed 2 and beneath thereof, an accommodating concave portion is formed, in which a tray carrying trolley 38 can be slidably accommodated. On top of the tray carrying trolley 38, a scope tray 39 for accommodating the endoscope 3 shown in FIG. 9 is mounted.

Then, the scope tray 39 accommodating the endoscope 3 which is sterilized or disinfected can be carried by the tray carrying trolley 38 and accommodated in the accommodating concave portion of the inspection bed 2. A surgeon can pull out the endoscope 3 from the scope tray 39 to use for endoscopy, and thereafter may reaccommodate the endoscope 3 in the scope tray 39. Later, the scope tray 39 accommodating the used endoscope 3 can be carried by the tray carrying trolley 38 to smoothly sterilize or disinfect the used endoscope 3.

As shown in FIG. 4, the AWS unit 4, for example, is provided with a scope connector 40. To the scope connector 40, a scope connector 41 (of the endoscope 3) is detachably connected, as shown in FIG. 8.

For this case, a more specific exterior shape of the scope connector 40 on the side of the AWS unit 4 is shown in FIGS. 5, 6A, and 6B. FIGS. 7A to 7E show a structure of the AWS adaptor 4 detachably attached to the scope connector 40 of the AWS unit 4. FIG. 8 shows an internal structure of the scope connector 40 on the side of the AWS unit 4 and the scope connector 41 on the side of the endoscope 3 in a connected status.

In fact, as shown in FIG. 6B, on a front surface of the AWS unit 4, an AWS adaptor attaching portion 40a in a concave form is provided. The AWS adaptor attaching portion 40a is attached with an AWS adaptor (channel connecting adaptor) 42 shown in FIGS. 7A to 7E to form the scope connector 40 which is connected with the scope connector 41 of the endoscope 3.

The AWS adaptor attaching portion 40a is provided with an electrical connector 43 for scope connection, an air supplying connector 44, and a pinch valve 45. To the AWS adaptor attaching portion 40a, an inner end surface of the AWS adaptor 42 is detachably attached. From an outer end surface of the AWS adaptor 42, the scope connector 41 of the endoscope 3 is connected.

The AWS adaptor 42 is shown in detail in FIGS. 7A to 7E. FIGS. 7A, 7B, and 7C show front, left, and right views of the AWS adaptor 42, respectively. FIGS. 7D and 7E show sectional views taken along A-A' and B-B' of FIG. 7A, respectively.

The AWS adaptor 42 has on a front surface thereof a concave portion 42a to which the scope connector 41 is inserted. This concave portion is provided inside with a through-hole 42b into which an electrical connector portion of the scope connector 41 is inserted. The electrical connector portion is then connected to the electrical connector 43 for scope connection provided to the AWS unit 4, the electrical connector 43 facing the inside of the through-hole 42b.

On a side below the through-hole 42b, an air and water supplying connector 42c and a suction connector 42d are provided, to which an air and water supplying ferrule 63 and a suction ferrule 64 in the scope connector 41 (see FIGS. 8 and 9) are connected, respectively.

On a proximal end surface side of the AWS adaptor 42, a concave portion 42f is provided for accommodating the pinch valve 45 protruding from the AWS adaptor attaching portion 40a.

As shown in FIG. 7E, the air and water supplying connector 42c provided to the AWS adaptor 42 communicates with an inner channel diverging into an air supplying ferrule 42e connected to the air supplying connector 44 of the AWS unit 4, and into a water supplying ferrule 46 protruding in a lateral direction. The suction connector 42d communicates with a channel curving in a lateral direction into a suction ferrule 47 protruding on a side surface, while also diverging on the half way in, for example, an upward direction into a relief channel 47a. The relief channel 47a passes on the way inside the pinch valve 45 and has an open upper end.

The relief channel 47a is normally set to a release status by the pinch valve 45, when a suction pump not shown forming a suction section is set to a constant operating status. The pinch valve 45 is driven when a suction operation is performed. Then, the pinch valve 45 is closed to unrelease the relief channel 47a to perform a suction operation.

As shown in FIG. 5 and the like, the water supplying ferrule 46 is connected with a water supplying tank 48, and the suction ferrule 47 is connected with a suction device (via a suction tube 49a with a suction tank 49b provided therein on the way). The water supplying tank 48 is connected to a water supplying tank connector 50 of the AWS unit 4. On a side above the scope connector 40 on the front surface of the AWS unit 4, an operation panel 4a is provided.

Next, referring to FIG. 9, a specific configuration of the endoscope 3 according to an embodiment of the present invention will be described.

As schematically described in FIG. 3, the endoscope 3 of the present embodiment comprises: the endoscope body 18 having the flexible inserting section 21 and the operating section 22 provided at the rear end thereof; and the tube unit 19 of the disposable type having at the proximal end thereof a general connector portion 52 that is detachably connected to a connector portion 51 (for connecting to the tube unit) provided near the proximal (front) end of the operating section 22 of the endoscope body 18. At a distal end of the tube unit 19 is provided the above-mentioned scope connector 41 that is detachably connected to the AWS unit 4.

The inserting section 21 comprises: the rigid tip end portion 24 provided to the end of the inserting section 21; the freely bendable bending portion 27 provided at the rear end of the tip end portion 24; and an elongate flexible portion (hose portion) 53 from a rear end of the bending portion 27 to the operating section 22. At a plurality of (specifically two) halfway positions of the flexible portion 53 are provided variable-rigidity actuators 54A, 54B each serving as a variable-rigidity mechanism called electropolymer artificial muscle (abbreviated as EPAM) capable of extending and contracting and changing rigidity when applied with a voltage. The effect of the capability to extend and contract and to change rigidity when applied with a voltage, possessed by the variable-rigidity actuator 54A, 54B, prevents the portion capable of changing rigidity from being restricted by a physical mechanism.

The tip end portion 24 of the inserting section 21 is provided with an illumination window which is attached inside thereof with, for example, a light emitting diode (abbreviated as LED) 56 serving as an illuminating section. The illumination light of the LED 56 is emitted in a forward direction through an illumination lens integrally attached to the LED 56, to illuminate a subject such as a diseased part. It is to be noted that the LED 56 may be an LED emitting a white light, or may be configured using a Red (R) LED, a Green (G) LED, and a Blue (B) LED emitting a light of red, green, and blue wavelength ranges, respectively. The light-emitting element forming an illuminating section is not limited to the LED 56, but may be formed using an LD (Laser Diode) or the like.

Adjacent to the illumination window, an observing window is provided which is attached with an object lens not shown. At an image focus position thereof, the CCD 25 incorporating a variable-gain function is placed to form an image-pickup section for picking up an object image. The CCD 25 of the present embodiment incorporates the variable gain function in the CCD element itself, and the variable gain function can easily vary the gain of the CCD output signal up to approximately several 100 times. Therefore, it is possible to obtain a bright image with a minor decrease in S/N even under the illumination light by the LED 56. Also, the LED 56 has better emission efficiency compared to a lamp, and thus can restrict increase of temperature near the LED 56.

Signal lines connected at each one end to the LED 56 and the CCD 25 and inserted through the inserting section 21 are connected at the other ends to a controlling circuit 57 which is provided in, for example, the operating section 22 and performs central control processing (integrated control processing).

In the inserting section 21, a plurality of UPD coils 58 are placed at a predetermined interval along a longitudinal direction thereof. The respective UPD coils 58 are connected with a signal line which is connected to the controlling circuit 57 through a UPD coil driving unit 59 provided in the operating section 22.

At four positions in a circumferential direction inside an envelope of the bending portion 27 are placed angle actuators 27a each formed by placing the EPAM in a longitudinal direction of the bending portion 27. The angle actuators 27a and the variable-rigidity actuators 54A, 54B are also connected to the controlling circuit 57 each through a signal line.

The EPAM used for the angle actuator 27a and the variable-rigidity actuators 54A, 54B can be contracted in a thickness direction and extended in a longitudinal direction as shown in FIG. 10B, by attaching electrodes on both sides of the EPAM having, for example, a planar shape as shown in FIG. 10A, and applying a voltage thereto. Also, the EPAM can vary the distortion amount proportionately, for example, to the approximate square of an electric field strength E by a voltage applied thereto, as shown in FIG. 10C.

When used as the angle actuator 27a, the EPAM may be formed in a wire shape or the like, and extended on one side and contracted on the other side, and thus can be bent likewise with a typical function with a wire. This extension and contraction can also vary the rigidity of the EPAM, which function is utilized in the variable-rigidity actuators 54A, 54B to make the rigidity of these portions variable.

In the inserting section 21, an air and water supplying channel 60a and a suction channel 61a are inserted through, and rear ends thereof provide a channel connector portion 51a opening at the connector portion 51. To the channel connector portion 51a is detachably connected a tube connector 52a in the general connector portion 52 at the proximal end of the tube unit 19.

The air and water supplying channel 60a is connected to the air and water supplying channel 60b inserted through the tube unit 19. The suction channel 61a is connected to the suction channel 61b inserted through the tube unit 19, while diverging in the tube connector 52a to externally open, so as to communicate with a treatment tool insertion opening (abbreviated as forceps opening) 62 into which a treatment tool such as a forceps can be inserted. When not used, the forceps opening 62 is closed with a forceps valve 62a.

Rear ends of the hand-side of the air and water supplying channel 60a and the suction channel 61b are the air and water supplying ferrule 63 and the suction ferrule 64, respectively, in the scope connector 41.

The air and water supplying ferrule 63 and the suction ferrule 64 are connected to the air and water supplying connector 42c and the suction connector 42d of the AWS adaptor 42, respectively, shown in FIGS. 6A, 6B, 7A and so on. Further, in the AWS adaptor 42, the air and water supplying connector 42c diverges into an air supplying channel and a water supplying channel, as shown in FIGS. 7a to 7E. As shown in FIG. 8, the air supplying channel is connected, via an electromagnetic valve B1 inserted thereto, to an air and water supplying pump 65 in the AWS unit 4, and the water supplying channel is connected to the water supplying tank 48. This water supplying tank 48 is also connected to the air and water supplying pump 65 via an electromagnetic valve B2 on the way. The air and water supplying pump 65 and the electromagnetic valves B1, B2 are connected to an AWS controlling unit 66 by a controlling line (driving line). The AWS controlling unit 66 controls the opening and closing operations of the electromagnetic valves B1, B2, to allow for supplying air and water.

In addition, as shown in FIG. 9, the operating section 22 of the endoscope body 18 is provided with a grasping section 68 to be grasped by a surgeon. On the circumference of the grasping section 68 are provided, for example, three scope switches SW1, SW2, SW3 for performing remote controls such as release and freeze, along a longitudinal axis of the operating section 22. The scope switches SW1, SW2, SW3 are each connected to the controlling circuit 57.

Further, on a sloping surface portion Sa slantingly formed as an top surface of an opposite side of the position of the operating section 22 where the scope switches SW1, SW2, SW3 are provided, a waterproof track ball 69 is provided which performs an angle operation (bending operation) and which is switched to make other remote-control settings and the like, at a position capable of operating the waterproof track ball 69 with a hand grasping the grasping section 68.

FIG. 11 shows a view in an arrow C in FIG. 9. As shown in FIG. 11, on both sides of the track ball 69 on the sloping surface portion Sa, two scope switches SW4, SW5 are provided at symmetrical positions in a left-and-right direction on both sides in a longitudinal direction of the operating section 22. The scope switches SW4, SW5 are usually assigned with functions of an air and water supply switch and a suction switch.

Supposing the operating section 22 of the endoscope 3 as viewed from the direction of the arrow C in FIG. 9 to be a front surface thereof, the track ball 69 is on a center line in the longitudinal direction of the operating section 22 or the inserting section 21, and the scope switches SW4, SW5 are symmetrically placed thereto. The three scope switches SW1, SW2, SW3 are placed on a rear surface side of the operating section 22 along the center line.

Thus, the operating section 22 comprises a plurality of inputting sections. To the operating section 22, various inputting sections such as the track ball 69 are provided symmetrically to the center axis in the longitudinal direction. Accordingly, when a surgeon grasps to operate the grasping section 68 of the operating section 22, a good operationality is similarly assured in grasping and operating the grasping section 68 with either the left or right hand.

The track ball 69 and the scope switches SW4, SW5 are also connected to the controlling circuit 57. The track ball 69 and the scope switches SW1 to SW5 correspond to the angle and remote-control manipulator 28 in FIG. 3. As will be described later, one or a plurality of the track ball 69 and the scope switches SW1 to SW5 serving as the inputting sections can be assigned with the rigidity-variation operating section. Also, the rigidity-variation operating section assigned to one or a plurality of the track ball 69 and the scope switches SW1 to SW5 is operated by a surgeon to make a direction to a rigidity-variation controlling section 93 to be described later. When receiving the direction, the rigidity-variation controlling section 93 varies the rigidity of the variable-rigidity actuators 54A, 54B.

Also, a power source line 71a and a signal line 71b extending from the controlling circuit 57 are contactlessly and electrically connected to a power source line 73a and a signal line 73b inserted through the tube unit 19, via contactless transmitting sections 72a, 72b formed to the connector portion 51 and the general connector portion 52 (see FIG. 12 for detail). The power source line 73a and the signal line 73b are connected to an electrical connector 74 including power source and signal contacts in the scope connector 41. It is to be noted that the side of the connector portion 51 at the contactless transmitting sections 72a, 72b is called, for example, a contactless transmitting unit 51b.

When a user connects the scope connector 41 to the AWS unit 4, the power source line 73a is connected to a power source unit 75 via the electrical connector 43 of the AWS unit 4, and the signal line 73b is connected to the a UPD unit 76, the sending and receiving unit 77, and the AWS controlling unit 66 (via the power source unit 75), as shown in FIG. 8. The sending and receiving unit 77 is connected to an antenna for wirelessly sending and receiving an electric wave.

FIG. 12 shows a configuration of a contactless connecting portion by the contactless transmitting sections 72a and 72b at the connector portions 51 and 52.

AC electric power supplied from the power source unit 75 through the power source line 73a inserted through the tube unit 19 is supplied to a primary coil C1a which is accommodated in an outer case of the connector portion 52 and which forms the contactless transmitting section 72a.

Inside an outer case of the connector portion 51, a secondary coil C1b is placed, so that the primary coil C1a and the secondary coil C1b are placed adjacent to each other to provide electromagnetic coupling with small amount of magnetic flux leak, thus forming a transformer T1.

With this electromagnetic coupling, the AC electric power supplied to the coil C1a is efficiently transmitted to the secondary coil C1b. The coil C1b is connected to a power source circuit 78 in the controlling circuit 57. The power source circuit 78 generates DC electric power required on the side of the controlling circuit 57.

The power source circuit 78 converts a DC voltage rectified through a rectifying diode D and a smoothing capacitor to a DC voltage required to operate the controlling circuit 57, by, for example, a three-terminal power source IC 79 and a smoothing capacitor, and then supplies the DC voltage to the controlling circuit 57.

The signal line 71b (forming a common signal-transmitting section) connected to the controlling circuit 57 is connected to a coil C2a forming the contactless transmitting section 72b. A coil C2b opposing and adjacent to the coil C2a is connected to a signal line 73b inserted through the tube unit 19. In other words, almost likewise with the case with the transformer T1, the contactless transmitting section 72b is formed by a transformer T2 in which the coils C2a and C2b electromagnetically couple.

Through the electromagnetically coupled coils C2a and C2b, a signal is transmitted from the side of the signal line 71b to the side of the signal line 73b and also in an opposite direction.

In the present embodiment, as will be described of the internal configuration in FIG. 13, the number of electric signal lines to be inserted through the tube unit 19 can be reduced by a configuration wherein the controlling circuit 57 centrally controls or manages the various inputting sections and an image-pickup section and the like. Also, even when functions provided in the endoscope 3 are modified, the signal line 73b in the tube unit 19 can be used as it is without any modification thereof. That is, the signal line 73b forms a common signal-transmitting section for transmitting various signals in a common manner.

As shown in FIG. 12, magnets M1 and M2 are placed so that different magnetic poles oppose to each other, adjacent to, for example, the transformer T2, so that the general connector portion 52 is detachably attached to the connector 51 when connected thereto, with the coils C1a and C1b, and coils C2a and C2b adjacently opposing to each other. Instead of the magnets M1 and M2, concave and convex portions fitting to each other for positioning may be provided to both of the connecting portions 51, 52.

Thus, one of the characteristics of the endoscope 3 of the present embodiment is the configuration of contactlessly and detachably connecting the endoscope body 18 to the tube unit 19.

FIG. 13 shows an electrical system configuration of the controlling circuit 57 and the like placed in the operating section 22 of the endoscope body 18, and of main components placed at various parts of the inserting section 21.

In the tip end portion 24 of the inserting section 21 shown on a lower left side of FIG. 13, the CCD 25 and the LED 56 are placed. In the bending portion 27 illustrated above the tip end portion 24 in the drawing, the angle actuator 27a (specifically the EPAM in the present embodiment) and an encoder 27c are placed.

In the flexible portion 53, a variable-rigidity actuator 54 and an encoder 54c are each placed (the variable-rigidity actuator 54, though specifically designates variable-rigidity actuators 54A, 54B utilizing the EPAM in the present embodiment, is shown simplified in one representative). In the flexible portion 53, the UPD coil 58 is also placed.

On the surface of the operating section 22 illustrated above the flexible portion 53 of the inserting section 21, the track ball 69, an air and water supply SW (SW4), a suction SW (SW5), and a scope SW (SW1 to 3) are placed. The track ball 69 is used for angle operation and selective operations of other functions and the like, as will be described.

These that are shown on the left side of FIG. 13 are connected via a signal line to the controlling circuit 57 provided to the operating section 22 shown on the right side of the drawing (the UPD coil driving unit 59 is in the operating section 22). The controlling circuit 57 performs driving control, signal processing and the like of those functions.

The controlling circuit 57 comprises a status managing section 81 configured by a CPU and the like for managing a control status, the status managing section 81 being connected to a status retaining memory 82 for retaining (memorizing) a status of each part. The status retaining memory 82 comprises a program storing memory 82a serving as a control information storing section. Program data serving as control information stored in the program retaining memory 82a is rewritten, to allow (the CPU configuring) the status managing section 81 to perform a control (management) corresponding to the modified configuration, even when the configuration shown in FIG. 13 is modified.

The status retaining memory 82 or at least the program retaining memory 82a is configured by, for example, a flash memory, an EEPROM, or the like, which is non-volatile and electrically rewritable, to make the program data easily modifiable through the status managing section 81.

The program data can be modified by, for example, sending a command for modifying the program data to the status managing section 81, via the signal line 71b, i.e., a wired sending and receiving unit 83 to be described below, and then after the command, sending program data to be rewritten from the side of the AWS unit 4. Version upgrade and the like can also be easily carried out via the signal line 71b.

To the status retaining memory 82 may be written and retained therein as below device type information unique to the each endoscope 3 and individual information corresponding to the usage status, to efficiently use the information. Specifically, the status retaining memory 82 retains, for example, device type information of the endoscope 3 (e.g., information on the type of the CCD 25, the length of the inserting section, and so on), as well as individual information for each endoscope 3 differing depending on the use status of endoscopy and the like (e.g., usage time (total or integrated usage time of the endoscope), the number of cleaning, adjusting value, maintenance history, and so on). These pieces of information are used to determine a system operation and to be provided to the user.

These pieces of information can also be externally edited outside such as from the endoscope system controlling device 5 and a cleaning apparatus not shown.

Thus, by combining the status retaining memory 82 with a conventional scope ID into a common use, the information (data) possessed by the scope ID can be efficiently utilized.

In addition, having the status retaining memory 82 can eliminate the need to separately provide a scope ID, provide a more sophisticated function than a conventional scope ID, and perform in a more detailed manner an appropriate setting, adjustment, management, processing, and so on.

Moreover, the status managing section 81 is connected to the wired sending and receiving unit 83 which (in the present embodiment) wiredly communicates with the AWS unit 4 (because the sending and receiving unit 83 corresponds to FIG. 2B, components thereof are shown attached with symbols in FIG. 2B, with the electrical connector 15 being the contactless transmitting sections 72*a*, 72*b* in the operating section 22, and being the electrical connector 74 at the end of the tube unit 19).

The status managing section 81 controls, via an illumination controlling section 84, an LED driving section 85 controlled by the illumination controlling section 84. The LED driving section 85 applies to the LED 56 a LED driving signal for making the LED 56 serving as the illuminating section emit light.

With the light emission of the LED 56, an object such as an illuminated diseased part forms, by the object lens not shown attached to the observation window, an image on an imaging surface of the CCD 25 placed at the imaging position of the lens, which is photoelectrically converted by the CCD 25.

The CCD 25 outputs signal electric charges photoelectrically converted and accumulated therein, as an image-pickup signal, with an application of a CCD driving signal from a CCD driving section 86 controlled by the status managing section 81. The image-pickup signal is converted from an analogue signal to a digital signal by an A/D converter (abbreviated as ADC) 87, and thereafter inputted to the status managing section 81, while the digital signal (image data) is stored in an image memory 88. The image data in the image memory 88 is sent to the data sending section 12' of the sending and receiving unit 83.

The image data is then transmitted from the electrical connector 15 (the contactless transmitting unit 51*b* in this embodiment) to the side of the AWS unit 4 via the signal line 73*b* in the tube unit 19, and further wirelessly sent from the AWS unit 4 to the endoscope system controlling device 5.

The output signal of the ADC 87 is sent to a brightness detecting section 89, and information of the image brightness detected by the brightness detecting section 89 is sent to the status managing section 81. With this information, the status managing section 81 performs light adjustment to appropriately control the illumination light amount of the LED 56, via the illumination controlling section 84.

The status managing section 81 controls an actuator driving section 92 via an angle controlling section 91 and performs the management for driving the angle actuator (EPAM) 27*a* by the actuator driving section 92. The driving amount of the angle actuator (EPAM) 27*a* is detected by the encoder 27*c* and controlled to match a value corresponding to a directed value.

The status managing section 81 controls the actuator driving section 94 via the rigidity-variation controlling section 93, and performs the management for driving the variable-rigidity actuator 54 by the actuator driving section 94. The driving amount of the variable-rigidity actuator 54 is detected by the encoder 54*c*, and is controlled to match a value corresponding to the directed value. The rigidity-variation controlling section 93 controls the variable-rigidity actuators 54A and 54B serving as the variable rigidity mechanism to vary the rigidity thereof.

To the status managing section 81 is inputted an operation signal from the trackball 69 and the like provided to the operating section 22, via a trackball displacement detecting section 95, the signal corresponding to an operating amount of the trackball 69.

Switch-pressing operations such as turning on the air and water supply SW, the suction SW, and the scope SW are detected by a switch-pressing detecting section 96, and the detected information is inputted to the status managing section 81. The EPAM has a characteristic in which a deformation due to an external force generates an electromotive force, and an EPAM placed on the opposite side of the driven EPAM may be used as an encoder.

The controlling circuit 57 comprises a power source transmitting and receiving section 97 and a power source generating section 98. The power source transmitting and receiving section 97 is specifically the contactless transmitting section 72*a* at the operating section 22. AC electric power transmitted to the power source generating section 98 is converted to DC electric power thereby. The power source generating section 98 corresponds to the power source circuit 78 in FIG. 11. The DC electric power generated by the power source generating section 98 supplies each portion inside the controlling circuit 57 with electric power required for the operation thereof.

FIG. 14 shows an internal configuration of the sending and receiving units 101 and an image processing unit 116 of FIG. 8 in the endoscope system controlling device 5.

The endoscope system controlling device 5 comprises, for example, the wireless sending and receiving units 101. Data such as an image signal wirelessly sent from the AWS unit 4 is captured by the antenna section 13, and sent to the data receiving section 14 to be amplified and subject to a demodulation processing. Operations of the data receiving section 14 are controlled by the data communication controlling section 11, and received data is sequentially accumulated in a buffer memory 102.

Image data in the buffer memory 102 is sent to the image processing section 103 for processing image data. Besides the image data from the buffer memory 102, also input to the image processing section 103 is character information from character generating section 105 for generating characters through a key input from a keyboard 104. Thus, to the image data, the character information can be superimposed and the like.

The image processing section 103 sends inputted imaged data and the like to an image memory controlling section 106, and then temporarily stores the image data and the like to an image memory 107 via the image memory controlling section 106 and records the image data to a recording medium 158.

The image memory controlling section 106 reads out and sends the image data temporarily stored in the image memory 107 to a digital encoder 108. The digital encoder 108 encodes and outputs the image data in a predetermined picture format to a D/A converter (abbreviated as DAC) 109. The DAC 109 converts a digital picture signal to an analogue picture signal. This analogue picture signal is further outputted from a picture output terminal to the observation monitor 6 via a line driver 110. On the observation monitor 6, an image corresponding to the image signal is displayed.

The image data temporarily stored in the image memory 107 is also read out and inputted to a DV data generating section 111, and the DV data generating section 111 generates DV data which is outputted from a DV data outputting terminal.

Moreover, the endoscope system controlling device 5 is provided with an image inputting terminal and a DV data inputting terminal. A picture signal inputted from the picture inputting terminal passes through a line receiver 112 and an ADC 113 to be converted to a digital signal. The digital signal is demodulated by a digital decoder 114 and then inputted to the image memory controlling section 106.

From DV data inputted to the DV data inputting terminal, image data is extracted (decoded) by an image data extracting section 115 and then inputted to the image memory controlling section 106.

The image memory controlling section 106 also causes the image memory 107 to temporarily store, or the recording medium 158 to record, a picture signal (image data) inputted from the picture inputting terminal or the DV data inputting terminal, or outputs the picture signal from the picture outputting terminal to the observation monitor 6.

In the present embodiment, image data picked up by the CCD 25 of the endoscope 3 and UPD image data generated by the UPD unit 76 are wirelessly inputted to the endoscope system controlling device 5 from the side of the AWS unit 4. The endoscope system controlling device 5 converts in a predetermined picture signal and outputs to the observation monitor 6 these pieces of image data. The endoscope system controlling device 5 may receive UPD coil position data instead of the UPD image data and generate the UPD image data in the image processing section 103.

FIG. 15 shows an internal configuration of the AWS unit 4.

Image data and operation data for a switch and the like inputted from the controlling circuit 57 of the endoscope 3 to the electrical connector 15 for the scope are outputted to the data communication controlling section 11 of the sending and receiving unit 77, and then sent from the antenna section 13 to the antenna section 13 of the endoscope system controlling device 5, along with the UPD image data from the UPD unit 76.

On the other hand, AWS-related information on the operation and the like of the air and water supply switch and the suction switch provided to the operating section 22 of the endoscope 3 is also sent to an air and water supply controlling section 122. The air and water supply controlling section 122 controls the operations of the pump 65 and an electromagnetic valve unit 124, corresponding to the AWS-related information. To the electromagnetic valve unit 124, the air and water supplying tubes 60b, 61b are connected via the AWS adaptor 42. To the electromagnetic valve unit 124 and the AWS adaptor 42, the water supplying tank 48 is connected. To the AWS adaptor 42 the suction tank 49b is connected.

Also, to the AWS unit 4, commercial power source is supplied, which is sent to a power source transmitting and outputting section 127 via an isolating transformer 126. The power source transmitting and outputting section 127 supplies AC power source isolated from the commercial power source, from the electrical connector 43 to the power source line 73a of the endoscope 3 connected with the electrical connector 43.

Transmitted electric power output of the above-mentioned power source transmitting and outputting section 127 is controlled by an electric power transmission controlling section 128 connected to the data communication controlling section 11.

In the endoscope system 1 including the present embodiment, when the power is turned on, various images are displayed on the observation monitor 6 as shown in FIG. 16A, for example. In this case, the observation monitor 6 is provided with: an information displaying area Rj for displaying patient information and the like; an endoscope image displaying area Ri; a UPD image displaying area Ru; a freeze image displaying area Rf; an angle shape displaying area Ra; and a menu displaying area Rm. On the menu displaying area Rm, a menu is displayed. The angle shape displaying area Ra displays an angle shape obtained by the encoder 27c detecting an angle operating amount of the angle actuator 27a.

Menus to be displayed on the menu displaying area Rm include a main menu shown in FIG. 16B. Displayed in the main menu are scope switch, angle sensitivity, inserting section rigidity, zoom, image emphasis, air supplying amount, along with an end item for directing an operation of ending the menu when directing an operation of returning to the previous menu screen.

When a user operates the trackball 69 and the like to move a selecting frame to the item of the scope switch for selection thereof, the frame of the scope switch item is thickly displayed to indicate the item is selected. By further pressing the trackball 69 to operate to determine the selection, functions to be assigned to the five scope switches SW1 to SW5 can be selected and set as shown in FIG. 16C.

Next, operations of the endoscope system 1 by such a configuration will be described.

As a preparation for carrying out endoscopy, the general connector portion 52 on the side of the disposable-type tube unit 19 is connected to the connector portion 51 of the operating section 22 of the endoscope body 18. In this case, the transformers T1, T2 forming the contactless transmitting sections 72a, 72b are connected mutually insulated, waterproofed, and electromagnetically. With this connection, the preparation of the endoscope 3 ends.

Next, the scope connector 41 of the tube unit 19 is connected to the connector 43 of the AWS unit 4. At this portion, connections of various channels, power source lines, signal lines, and optical connections are completed in one connecting operation by one-touch connection. It is not necessary to make a connection for each of the various channels and electric connectors and the like each time as in a conventional endoscope system.

The user also connects the AWS unit 4 to the coil unit 8, and the endoscope system controlling device 5 to the observation monitor 6. Further, by connecting the endoscope system controlling device 5 to the image recording unit 7 and the like if necessary, the setup for the endoscope system 1 is completed.

Next, power sources of the AWS unit 4 and the endoscope system controlling device 5 are turned on. Then, the each portion in the AWS unit 4 becomes operable, turning the power source unit 75 capable of supplying electric power to the side of the endoscope 3 via the power source line 75 and the like.

Operations of the AWS unit 4 and the endoscope 3 when activated in this case will be described referring to FIGS. 17 and 18.

The electric power transmission controlling section 128 in the power source unit 75 of the AWS unit 4 shown in FIG. 15, on starting an activating processing, turns the status of the power source transmitting and outputting section 127 to stopping, that is, turning off electric power supply, in the first step S1 as shown in FIG. 17.

Thereafter, after a monitor timer is turned on in step S2, the status of the power source transmitting and outputting section 127 is turned to that of supplying electric power, that is, the electric power supply is turned on as shown in step S3. Thus, with the power source transmitting and outputting section 127 being turned to the status of supplying electric power, this electric power passes through the power source line 73a in the tuber unit 19 and further the contactless transmitting section 72a, so that AC electric power is supplied to the power source generating section 98 in the controlling circuit 57 in the operating section 22.

Then, as shown in step S4, the electric power transmission controlling section 128 comes into to a status of waiting for receiving an activation message from the side of the endoscope 3 via the signal line 73b in the tube unit 19. If no activation message is received, then the electric power transmission controlling section 128 determines whether or not the monitor timer is up, as shown in step S5. If the timer is not up, then the procedure returns to step S4, and if the timer is up, then the procedure returns to the first step S1.

In contrast, if an activation message is received, the electric power transmission controlling section 128 turns off the time measurement of the monitor timer, as shown in step S6. Then, as shown in step S7, the electric power transmission controlling section 128 publishes a continuation message to end this activating processing.

On the other hand, when AC electric power is supplied to the power source generating section 98, the controlling circuit 57 in the endoscope 3 is supplied with an electric power needed for the operation in the controlling circuit 57, thus starting the activating processing. Then, in the first step S11, the status managing section 81 shown in FIG. 13 waits for the electric power supply voltage of the power source generating section 98 to stabilize.

If the electric power supply voltage has stabilized, then in next step S12, the status managing section 81 performs system initialization for each portion of the controlling circuit 57. After this system initialization, as shown in step S13, the status managing section 81 sends an activation message to the electric power transmission controlling section 128, via the sending and receiving unit 83 and further the signal line 73b in the tube unit 19.

After sending this activation message, as shown in step S14, the status managing section 81 comes to a status of waiting for receiving a continuation message from the side of the electric power transmission controlling section 128. If a continuation message is received, then the status managing section 81 ends the activating processing. If no continuation message is received, then as shown in step S15, the status managing section 81 returns to step S13 to republish an activation message if conditions for ending retrial (e.g., that of the predetermined number of retrying times) are not satisfied, or ends in an error if the conditions for ending retrial are satisfied.

When the above-mentioned activating processing has normally ended, the CCD 25 starts picking up an image, allowing a user to perform air and water supply, suction, angle operation, rigidity varying operation, and so on, using the inputting sections of the operating section 22.

A representative processing operation regarding to these operations will be described with FIGS. 19 to 22. FIG. 19 shows contents of an image-pickup control processing.

As shown in FIG. 19, when the image-pickup processing starts, the endoscope 3 obtains image-pickup data, as shown in step S21. Specifically, under the management (control) of the status managing section 81, the LED 56 emits light, and the CCD driving section 86 starts an operation for driving the CCD 25. An image-pickup signal picked up by the CCD 25 is converted to a digital signal (image-pickup data) by the ADC 87. The image-pickup data (image data) is sequentially stored in the image memory 88 and image-pickup data is thus obtained.

The obtained image data is sequentially sent as shown in step S22. The image data read out from the image memory 88 is wiredly sent from the sending and receiving unit 83 to the AWS unit 4. Then, the image data is wirelessly sent from the sending and receiving unit 77 of the AWS unit 4 to the side of the endoscope system controlling device 5. In the endoscope system controlling device 5, the image data is converted to an image signal to be displayed on the observation monitor 6.

Further, the image-pickup data of the ADC 87 is inputted to the brightness detecting section 89. As shown in step S23, the brightness detecting section 89 detects a brightness of the image-pickup data by, for example, calculating an average value of luminance data of the image-pickup data in an appropriate time.

Detection data of the brightness detecting section 89 is inputted to, for example, the status managing section 81, to determine whether or not the detection data has a specified brightness (step S24). If the detection data has the specified brightness, the image-pickup processing ends, and proceeds to a next image-pickup processing.

On the other hand, if it is not determined in step S24 that the detection data has the specified brightness, then the status managing section 81 sends a directing signal (controlling signal) for adjusting illumination light to the illumination controlling section 84, and then the illumination controlling section 84 performs illumination light amount adjustment, as shown in step S25. For example, the illumination controlling section 84 adjusts illumination light amount by, for example, increasing or decreasing a driving current for making the LED 56 emit light. The illumination controlling section 84 returns the adjustment result to the status managing section 81.

Accordingly, the status managing section 81 determines with the adjustment result information whether or not the result is within a brightness range adjustable by the illumination controlling section 84. If the brightness could be adjusted by the illumination controlling section 84, then the image-pickup processing control ends without performing the processing of step S27. In contrast, if the result is out of the brightness range adjustable by the illumination controlling section 84, then as shown in step S27, the status managing section 81 outputs a CCD gain adjusting signal to the CCD driving section 86, to adjust the brightness of the image-pickup data by adjusting the gain of the CCD 25. Then, this image-pickup processing ends.

Next, an air and water supply processing of FIG. 20 will be described. As shown in FIG. 11, functions of the air and water supply switch and the suction switch are typically assigned to the both side of the trackball 69 of the operating section 22.

When the air and water supply processing starts, as shown in step S31 of FIG. 20, the status managing section 81 of the controlling circuit 57 obtains status data of the air and water supply switch.

The operation of the air and water supply switch is detected by the switch-pressing detecting section 96 shown in FIG. 13, and with an input of the detection result information, the status managing section 81 obtains status data of the air and water supply switch.

Then, as shown in step S32, the status managing section 81 determines status change of the air and water supply switch. If it is determined in step S32 that there is a status change of the air and water supply switch, then as shown in step S33, the status managing section 81 sends air and water supply controlling data corresponding to a direction by the air and water supply switch operated by the user, to the side of the AWS unit 4 via the sending and receiving unit 83.

The air and water supply controlling section 122 in the AWS unit 4 performs a control operation for the pump 65 and an electromagnetic valve unit 124, in response to the air and water supply controlling data. Then, this operation of air and water supply processing ends. In contrast, if it is determined in step S32 that there is no status change of the air and water supply switch, then the status managing section 81 ends the operation of the air and water supply processing, without processing step S33. It is to be noted that because suction processing is almost the same as the air and water supply processing, description thereof is omitted.

Next, a processing of angle operation control will be described referring to FIG. 21. When the processing of angle operation control starts, the status managing section 81 determines whether or not angle control is validated, as shown in step S41.

In the present embodiment, the status managing section 81 determines whether or not angle control is validated, based on whether or not the track ball 69 is pressed. Specifically, the status managing section 81 can detect a displacing operation and a pressing operation, with an output of the trackball displacement detecting section 95. While the track ball 69 is pressed, the angle control is turned off.

The status managing section 81 determines whether or not the angle control is validated, with an output of the trackball displacement detecting section 95.

Then, if it is determined that the angle control is not validated, the processing moves to step S45 to retain a previous command value. In contrast, if it is determined that the angle control is validated, the processing proceeds to step S42, and the status managing section 81 obtains status data by the operation of the trackball 69. In the following step S43, the status managing section 81 determines whether or not there is a further status change, with an output of the trackball displacement detecting section 95.

In this case, if it is determined that there is no status change, then the processing moves to step S45. On the contrary, if it is determined that there is a status change, then in the next step S44, the status managing section 81 calculates a command value corresponding to the rotation direction and the rotation amount of the trackball 69.

After the processings of step S44 or S45, as shown in step S46, the status managing section 81 sends the command value to the actuator driving section 92 via the angle controlling section 91, and servo-processes the angle actuator.

In other words, the actuator driving section 92 drives the angle actuator based on the command value to obtain an angle status (bending angle) corresponding to the command value. At this time, an angle status of the angle actuator is detected by the encoder, and the actuator driving section 92 drives the angle actuator so that the value detected by the encoder match the command value. Thus, the angle control processing ends.

FIG. 21 also shows processing operations (steps S47 and S48) for a case where a contact sensor is provided in the servo-processing of step S46.

Next, with reference to FIG. 22, a control processing of the rigidity varying operation will be described. This control processing performs a control processing basically similar to that in FIG. 21.

When the control processing of the rigidity varying operation starts, the status managing section 81 determines whether or not the rigidity varying operation is validated, as shown in step S51.

Specifically, rigidity of the inserting section is assigned to the scope switches SW1 to SW5 in the main menu as shown in FIG. 16B, and the status managing section 81 determines whether or not the scope switch for the rigidity of the inserting section is pressed and validated.

If it is determined that the rigidity varying control is not validated, then the processing proceeds to step S55 to retain the previous command value. In contrast, if it is determined that the rigidity varying control is validated, then the processing proceeds to step S52, and the status managing section 81 obtains status data of the trackball 69 by an operation thereof.

Then, in a next step S53, the status managing section 81 determines whether or not there is a further status change by an output of the trackball displacement detecting section 95.

In this case, if it is determined that there is no status change, then the status managing section 81 proceeds to step S55. On the contrary, if it is determined that there is a status change, then in the next step S54, the status managing section 81 calculates a command value corresponding to the rotation direction and the rotation amount of the trackball 69.

After the processing of step S54 or S55, as shown in step S56, the status managing section 81 sends the command value to the actuator driving section 94 via the rigidity-variation controlling section 93, and servo-processes the variable-rigidity actuator 54A or 54B.

In other words, the actuator driving section 94 drives the variable-rigidity actuator 54A or 54B based on the command value to obtain a target rigidity corresponding to the command value. At this time, the encoder 54c detects the status of the variable rigidity of the variable-rigidity actuator 54A or 54B, and the actuator driving section 94 drives the variable-rigidity actuator 54A or 54B to make the value detected by the encoder 54c reach target rigidity.

In step S57 in the middle of such a servo-processing, the rigidity-variation controlling section 93 or the status managing section 81 determines whether or not the target rigidity is within a variable range of the variable-rigidity actuator 54A or 54B by the actuator driving section 94. If the target rigidity is out of this range, the variable rigidity control processing ends.

Further, in step S57, if the target rigidity is within the variable range of the variable-rigidity actuator 54A or 54B, then in the next step S58, the rigidity-variation controlling section 93 or the status managing section 81 determines whether or not the target rigidity has been reached. If the target rigidity has not been reached, then the processing returns to step S56 to continue the servo-processing. If the target rigidity is thus reached, the variable rigidity control processing ends.

Also, the UPD unit 76 detects the positions of the UPD coils 58 placed in the inserting section 21 of the endoscope 3 by using the UPD coil unit 8, calculates the insertion shape of the inserting section 21, and then displays an image of the insertion shape, i.e., a UPD image, on the display screen of the observation monitor 6.

FIGS. 23A to 23B are each shown with a right-side menu screen and a left-side UPD image corresponding to each other, in such a manner that, when the user uses the menu screen to select and set a rigidity of the variable-rigidity actuators 54A, 54B, the rigidity portions of the variable-rigidity actuators 54A, 54B provided at a plurality of positions (two positions in the embodiment) are each displayed in a color corresponding to the set rigidity, so that the rigidity of the rigidity portions are easily recognized.

FIG. 23A shows a display status of the main menu, in which the user selects variable inserting section rigidity. Because, in this case, the UPD image is right before the variable inserting section rigidity is selected, zones A, B of the variable-rigidity actuators 54A, 54B are displayed not distinguished from the other sections than the sections A, B.

When the variable inserting section rigidity is selected as shown in FIG. 23B, zone ranges of rigidity to be set for the zones A, B of the variable-rigidity actuators 54A, 54B at the two positions are shown. A rigidity setting screen is displayed for setting which rigidity from a flexible status to a rigid status in the zones A, B, and positions of current rigidities are indicated with circles. In this case, the flexible to rigid rigidities are respectively displayed in a different displaying color.

Therefore, in a corresponding UPD images, the portions of the variable-rigidity actuators are each color-displayed in displaying colors corresponding to the rigidities to which the variable-rigidity actuators are set. In the status of FIG. 23B, the rigidity zones are set close to flexible, and the zones A, B of the variable-rigidity actuators 54A and 54B are displayed in yellow in the UPD image.

FIG. 23C shows a case in which, for example, the rigidity of the zone B of the variable-rigidity actuator 54B is set, in the status of FIG. 23B, to a rigidity close to the middle. In this case, the zone B of the variable-rigidity actuator 54B is displayed in green in the UPD image.

FIG. 23D shows a case in which, for example, the rigidity of the zone B of the variable-rigidity actuator 54B is set, in the status of FIG. 23B or 23C, to a rigid rigidity (rigid value). In this case, the section B of the variable-rigidity actuator 54B is displayed in blue in the UPD image.

By providing a display in this manner, the user can freely set rigidities of the variable-rigidity actuators 54A, 54B. Also, the user can easily distinguish the rigidity of the variable-rigidity actuators 54A, 54B because the portions of the zones A, B of the variable-rigidity actuators 54A, 54B thus set are displayed in displaying colors corresponding to the set rigidities.

Further, the shape of the inserting section 21 is displayed with the UPD coils 58, which allows the user to easily perform an inserting operation and the like of the inserting section 21.

Next, referring to FIGS. 24 and 25 are described processing contents on the sides of the endoscope 3 and the endoscope system controlling device 5 in a human interface achieving a remote control by the user. In FIGS. 24 and 25, the human interface is abbreviated as HMI.

As shown in FIG. 24, when a human interface processing starts, the status managing section 81 waits for an angle validating switch to be turned off, i.e., waits for the trackball 69 to be pressed to turn off the angle validating switch.

Then, when the angle validating switch is turned off, the status managing section 81 publishes a GUI (Graphical User Interface) display message, as shown in the next step S62. The GUI display message is wirelessly sent from the endoscope 3 to (a controlling CPU) in a system controlling unit 117 of the endoscope system controlling device 5, via the AWS unit 4.

After publishing the GUI display message, in the next step S63, the status managing section 81 comes to a status of waiting for receiving a GUI display completion message from the side of the endoscope system controlling device 5. When the GUI display completion message can not be received, the status managing section 81 proceeds to step S64 to determine whether or not a condition for ending retrial is met. If the condition for ending retrial is not met, then the process returns to step S63. If the condition for ending retrial is met on the contrary, then the process ends in error.

In the processing of step S63, if the display completion message is received, the status managing section 81 proceeds to step S65 to determine whether or not the angle validating switch is turned on. If the angle validating switch is turned on, the status managing section 81 publishes a GUI ending message as shown in step S66.

Likewise with the case of the GUI display message, the GUI ending message is wirelessly sent from the endoscope 3 to the endoscope system controlling device 5 via the AWS unit 4. After publishing the GUI ending message, in the next step S67, the status managing section 81 comes to a status of waiting for receiving a GUI display ending message from the side of the endoscope system controlling device 5. If the GUI display ending message is received, the status managing section 81 ends this human interface processing.

In contrast, if the GUI display ending message can not be received, the status managing section 81 proceeds to step S68 to determine whether or not a condition for ending retrial is met. If the condition for ending retrial is not met, the processing returns to step S66. If the condition for ending retrial is met on the contrary, the processing ends in error.

If the angle validating switch is not turned on in step S65, the processing moves to that in a menu screen in step S69. In this step S69, the status managing section 81 determines whether or not there is a status change in the trackball 69, based on whether or not an output of the trackball displacement detecting section 95 has a change amount equal to or more than a threshold value.

If it is determined that there is a status change in the trackball 69, the status managing section 81 obtains status data (change data) of the trackball 69, as shown in step S70.

In this case, the user can select and direct a function of a desired item with a cursor moving corresponding to the operation of the trackball 69 in the main menu screen of FIG. 16B.

Then, as shown in step S71, the status managing section 81 sends status data corresponding to the operation of the trackball 69 by the user. This status data is sent as packet data from the endoscope 3 to the endoscope system controlling device 5 via the AWS unit 4, in sync with the image-pickup data of the CCD 25. After sending the status data, the processing returns to that of step S65.

If it is determined that there is no status change in step S69, then as shown in step S72, the status managing section 81 determines whether or not there is a status change in a switch (switch SW1 to SW5), based on a detection output by the switch-pressing detecting section 96.

If it is determined that there is no status change in the switches in step S72, the status managing section 81 returns to step S65. If it is determined that there is a status change in the switches on the contrary, the status managing section 81 obtains switch pressing status data as shown in step S73, and further sends the obtained switch pressing status data in the next step S74 and returns to the processing of step S65.

On the other hand, when a human interface processing starts as shown in FIG. 25, the CPU of the system controlling unit 117 of the endoscope system controlling device 5 comes to a status of waiting for receiving a GUI display message from the side of the endoscope 3 in the first step S81. This CPU waits for wirelessly receiving a GUI display message via the sending and receiving unit 101 of FIG. 8 or 14.

Then, as shown in step S82, on receiving a GUI display message, the CPU of the system controlling unit 117 performs a control processing of the GUI display. That is, the CPU performs a control for providing the GUI display, with respect to the image processing unit 116.

After the processing for the GUI display in step S82, the CPU publishes a display completion message as shown in step S83. The CPU sends the display completion message via the sending and receiving unit 101. In the next step S84, the CPU determines whether or not a GUI ending message has been received from the side of the endoscope 3. If the GUI ending message has been received, the CPU performs a processing for ending the GUI display in step S85, and then in the next step S86, publishes a GUI display ending message before ending the processing of this human interface.

If in step S84 the GUI ending message has not been received, then the CPU proceeds to step S87 to determine whether or not there is a change in reception data of the trackball 69. The determination on whether or not there is a change in the reception data of the trackball 69 is carried out when receiving a result of determination on status change of the trackball 69 by the side of the endoscope 3. If there is a change in the reception data, status data of the trackball 69 is obtained as shown in step S88. Further, in the next step S89, the CPU moves the cursor by an amount corresponding to the obtained status data (change data) of the trackball 69, and then returns to the processing of step S84.

If in the processing of step S87, it is determined that there is no change in the reception data of the track ball 69, then as shown in step S90, the CPU determines whether or not there is a change in the switch reception data, based on reception data received of the sent data of the determination result on the side of the endoscope 3.

If it is determined that there is a change in the switch reception data, then as shown in step S91, the CPU obtains switch pressing status data from information sent from the side of the endoscope 3. Further, as shown in step S91, the CPU performs a processing for performing a function assigned to the switch pressed, and then returns to the processing of step S84. Also when there is no change in reception data of the switch in step S90, the processing returns to step S84.

According to the endoscope 3 of the present embodiment forming the endoscope system 1 performing such an operation, cleaning, sterilizing and the like of the endoscope body 18 can be easily performed, by making the endoscope 3 separable into the endoscope body 18 and the tube unit 19 at the operating section 22, and using the tube unit 19 of the disposable type.

That is, the air and water supplying channel 60a and the suction channel 61a in the endoscope body 18 can be made much shorter compared with the case of a conventional example in which universal cables corresponding to the tube unit 19 are integrally formed, and therefore can be easily cleaned and sterilized.

Also, in the case of a conventional example in which the universal cables corresponding to the tube unit 19 are integrally formed, the universal cables are connected with the operating section 22 in a curving manner. While in the present embodiment, the channel connector portion 51a only slightly curving is provided at the connector portion 51 of the operating section 22, while the other portions thereof are the air and water supplying channel 60a and the suction channel 61a extending in an approximately linear manner. Thus, it becomes possible to perform processes such as cleaning, sterilizing, and drying the channels, easily and in a short period of time. Accordingly, a status capable of performing endoscopy can be set in a short period of time.

In addition, in the present embodiment, because the endoscope body 18 and the tube unit 19 are structured to contactlessly and detachably connect, repeated cleaning and sterilizing of the endoscope body 18 will not cause a faulty conduction and the like of a contact in a non-contactless case, and thus can increase reliability.

Further, in the present embodiment, the operating section 22 is provided with many inputting sections such as an angle operating section, an air and water supply operating section, a suction operating section, a rigidity-variation operating section, a freeze operating section, and a release operating section, and is configured to integrally (centrally) control these inputting sections by the controlling circuit 57 provided in the operating section 22. The controlling circuit 57 is also configured to integrally control the light-emitting section for emitting illumination light for picking up an image and the image-pickup section for picking up an image, along with each of the above-mentioned inputting sections.

In this manner, the present embodiment is configured to integrally control the various functions provided in the endoscope body 18 by the controlling circuit 57 provided in the operating section 22, and also to integrally control the various functions of the inputting sections for the AWS unit 4 connected to the endoscope body 18 and for the endoscope system controlling device 5 wirelessly sending and receiving information. Therefore, the user (more specifically, the surgeon) can freely perform various operations with the various inputting sections provided to the operating section 22, thus considerably improving operationality.

In particular, in the present embodiment, by providing the controlling circuit 57 for performing an integral control in the operating section 22, image data picked up and obtained by the CCD 25 and various signals caused by the inputting sections are packetized, for example, and transmitted from the controlling circuit 57 in a common manner through a pair of signal lines 71b. Therefore, the number of electrical signal lines can be decreased (specifically, the signal lines can be decreased to two signal lines for transmitting signals and two power source lines for transmitting electric power, and in addition, the signal lines can be decreased to three lines by commonly using each one of the signal lines and the power source lines).

Accordingly, the number of signal lines required to be inserted through the tube unit 19 connected to the connection portion of the operating section 22 can also be decreased, which makes the side of the tube unit 19 disposable.

Furthermore, by decreasing the number of signal lines to be inserted through the tube unit 19, the tube unit 19 can easily be decreased in diameter and be bent, thereby improving operationality for a user in operating the endoscope.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope comprising an inserting section and an operating section, wherein
the inserting section comprises at a plurality of positions a variable-rigidity mechanism capable of varying rigidity when applied with a voltage, and
the operating section comprises:
a rigidity-variation controlling section for varying rigidity by controlling the variable-rigidity mechanism;
a rigidity-variation operating section for making a direction for varying rigidity to the rigidity-variation controlling section, and
an endoscope shape detecting section for displaying an image of a shape of the inserting section on a display section,
wherein a rigidity of the variable-rigidity mechanism is displayed on the display section along with the image of the shape of the inserting section.

2. The endoscope as claimed in claim 1, wherein the operating section comprises a plurality of inputting sections and a selecting mechanism, and a surgeon can assign a function of the rigidity-variation operating section to one of the plurality of inputting sections by operating the selecting mechanism and selecting one of the plurality of inputting sections.

3. The endoscope as claimed in claim 2, wherein the variable-rigidity mechanism extends in a longitudinal direction when applied with a voltage.

4. The endoscope as claimed in claim 3, wherein the variable-rigidity mechanism contracts in a thickness direction when applied with a voltage.

5. The endoscope as claimed in claim 4, wherein a distortion amount of the variable-rigidity mechanism is proportional to the approximate square of an electric field strength based on a voltage applied to the variable-rigidity mechanism.

6. The endoscope as claimed in claim 5, wherein the variable-rigidity mechanism comprises an electropolymer artificial muscle.

7. The endoscope as claimed in claim 4, wherein the variable-rigidity mechanism comprises an electropolymer artificial muscle.

8. The endoscope as claimed in claim 3, wherein a distortion amount of the variable-rigidity mechanism is proportional to the approximate square of an electric field strength based on a voltage applied to the variable-rigidity mechanism.

9. The endoscope as claimed in claim 8, wherein the variable-rigidity mechanism comprises an electropolymer artificial muscle.

10. The endoscope as claimed in claim 3, wherein the variable-rigidity mechanism comprises an electropolymer artificial muscle.

11. The endoscope as claimed in claim 2, wherein the variable-rigidity mechanism contracts in a thickness direction when applied with a voltage.

12. The endoscope as claimed in claim 11, wherein a distortion amount of the variable-rigidity mechanism is proportional to the approximate square of an electric field strength based on a voltage applied to the variable-rigidity mechanism.

13. The endoscope as claimed in claim 12, wherein the variable-rigidity mechanism comprises an electropolymer artificial muscle.

14. The endoscope as claimed in claim 11, wherein the variable-rigidity mechanism comprises an electropolymer artificial muscle.

15. The endoscope as claimed in claim 2, wherein a distortion amount of the variable-rigidity mechanism is proportional to an approximate square of an electric field strength based on a voltage applied to the variable-rigidity mechanism.

16. The endoscope as claimed in claim 15, wherein the variable-rigidity mechanism comprises an electropolymer artificial muscle.

17. The endoscope as claimed in claim 2, wherein the variable-rigidity mechanism comprises an electropolymer artificial muscle.

18. The endoscope as claimed in claim 2, wherein the selecting mechanism comprises a trackball.

19. The endoscope as claimed in claim 2, wherein the plurality of inputting sections comprise at least one scope switch.

20. The endoscope as claimed in claim 2, wherein the plurality of inputting sections are provided symmetrically with respect to a center axis in a longitudinal direction of the operating section.

21. The endoscope as claimed in claim 1, wherein the rigidity-variation controlling section performs servo-processing to the variable-rigidity mechanism.

22. The endoscope as claimed in claim 1, wherein the rigidity-variation controlling section ends a processing of variable-rigidity control, when detecting a deviation from a variable rigidity range of the variable-rigidity mechanism.

23. The endoscope as claimed in claim 1, wherein the inserting section comprises a flexible portion, and the variable-rigidity mechanism is provided to the flexible portion.

24. The endoscope as claimed in claim 1, wherein the plurality of positions are two positions.

* * * * *

UNITED STATES PATENT AND TRADEMARK OFFICE
CERTIFICATE OF CORRECTION

| | | |
|---|---|---|
| PATENT NO. | : 7,896,801 B2 | Page 1 of 1 |
| APPLICATION NO. | : 11/585300 | |
| DATED | : March 1, 2011 | |
| INVENTOR(S) | : Uchimura et al. | |

It is certified that error appears in the above-identified patent and that said Letters Patent is hereby corrected as shown below:

Title Page should read

(57)                      ABSTRACT

An endoscope is provided wherein a variable rigidity portion is not restricted by a physical mechanism, and which allows a surgeon, in performing a rigidity varying operation, to operate the rigidity varying operation along with other operations without releasing inputting sections. The endoscope of the invention includes an inserting section and an operating section. The inserting section has variable-rigidity actuators. The operating section has a rigidity-variation controlling section, a trackball, and scope switches. The endoscope further includes a shape detecting section for displaying an image of a shape of the inserting section. The rigidity of the variable rigidity actuators is displayed on a display along with the image of the shape of the inserting section.

Signed and Sealed this
Fourteenth Day of June, 2011

David J. Kappos
*Director of the United States Patent and Trademark Office*